US006335364B1

(12) United States Patent
Uckun et al.

(10) Patent No.: US 6,335,364 B1
(45) Date of Patent: Jan. 1, 2002

(54) SYNTHETIC SPIROKETAL PYRANES AS POTENT ANTI-CANCER AGENTS

(75) Inventors: Faith M. Uckun, White Bear Lake; Chen Mao, St. Paul; He Huang, New Brighton, all of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/352,648

(22) Filed: Jun. 29, 1999

Related U.S. Application Data

(60) Provisional application No. 60/091,002, filed on Jun. 29, 1998.

(51) Int. Cl.$^7$ ............... A61K 31/35; C07D 311/00

(52) U.S. Cl. ............... 514/460; 514/451; 549/343

(58) Field of Search ............... 549/343; 514/451, 514/460

(56) References Cited

U.S. PATENT DOCUMENTS

| | | | | |
|---|---|---|---|---|
| 3,099,662 A | * | 7/1963 | Wasson et al. ............... | 549/343 |
| 4,820,758 A | * | 4/1989 | Nelson ............... | 549/214 |
| 5,322,854 A | * | 6/1994 | Isono et al. ............... | 514/451 |

FOREIGN PATENT DOCUMENTS

EP  0 491 956 A1  7/1992

OTHER PUBLICATIONS

Avila, J., (1992), *Life Sci.*, 50(5): 327–334 "Microtubule Functions".
Bai, R. et al., (Oct. 1993), *Molecular Pharmacology*, 44(4):757–766 "Spongistatin 1, a Highly Cytotoxic, Sponge—Derived, Marine Natural Product that Inhibits Mitosis, Microtubule Assembly, and the Binding of Vinblastine to Tubulin".
Bai, R. et al., (Aug. 1, 1995), *Biochemistry*, 34(30):9714–9721 "The Spongistatins, Potently Cytotoxic Inhibitors of Tubulin Polymerization, Bind in a Distinct Region of the Vinca Domain".
Böhm, H., (Dec. 1992), *J. Comput. Aided Mol. Des.*, 6(6):593–606 "LUDI: rule—based automatic design of new substituents for enzyme inhibitor leads".
Böhm, H., (Jun. 1994), *J. Comput. Aided Mol. Des.*, 8(3):243–256 "The development of a simple empirical scoring function to estimate the binding constant for a protein—ligand complex of known three—dimensional structure".
Cohen, T. et al., (Mar. 2, 1990), *J. Org. Chem.*, 55(5):1528–1536 "Synthetically Useful β—Lithioalkoxides from Reductive Lithiation of Epoxides by Aromatic Radical Anions".
Connolly, M., (Aug. 19, 1983), *Science*, 221(4612):709–713 "Solvent—Accessible Surfaces of Proteins and Nucleic Acids".

Corey, E. et al., (Aug. 23, 1972), *J. Am. Chem. Soc.*, 94(17):6190–6191 "Protection of Hydroxyl Groups as tert—Butyldimethylsilyl Derivatives".
Danishefsky, S. et al., (Dec. 23, 1987), *J. Am. Chem. Soc.*, 109(26):8117–8119"The Total Synthesis of the Aglycon of Avermectin $A_{1a}$".
Downing, K. et al., (Feb. 1998), *Curr. Opin. Cell. Biol.*, 10(1):16–22 "Tubulin and microtubule structure".
Hyman, A. et al., (Aug. 1998), *J Cell Sci.* 111(15):2077–2083 "The role of nucleation in patterning microtubule networks".
Kozielski, F. et al., (Feb. 12, 1998), *Curr Biol.*, 8(4):191–198 "A model of the microtubule—kinesin complex based on electron cryomicroscopy and X–ray crystallography".
Luty, B. et al., (Apr. 1995), *J. Comp. Chem.*, 16(4):454–464 "A Molecular Mechanics/Grid Method for Evaluation of Ligand —Receptor Interactions".
Makabe, H. et al., (1996), *Heterocycles*, 43(10):2229–2248 "Total Synthesis of (8'R)—And (8'S)—Corossoline".
Mao, C. et al., (1998), *Bioorganic & Medicinal Chemistry Letters*, 8:2213–2218 "Structure—Based Design of N–[2–(1–Piperidinylethyl)]–N'–[2–(5–Bromopyridyl)]–Thiourea and N–[2–(1–Piperazinylethyl)]–N'–[2–(5–Bromopyridyl)]–Thiourea as Potent Non–Nucleoside Inhibitors of HIV–1 Reverse Transcriptase".
Nogales, E. et al., (Jan. 8, 1998), *Nature*, 391(6663):199–202 "Structure of the αβ tubulin dimer by electron crystallography".
Nogales, E., (Jan. 8, 1999), *Cell*, 96(1):79–88 "High—Resolution Model of the Microtubule".
Nicholls, A. et al., (1991), *Proteins, Structure, Function and Genetics*, 11:281–296 "Protein Folding and Association: Insights From the Interfacial and Thermodynamic Properties of Hydrocarbons".
Paterson, I. et al., (Nov. 18, 1996), *Tetrahedron Lett.*, 37 (47):8581–8584 Studies in Marine Macrolide Synthesis: Stereocontrolled Synthesis of the AB—Spiroacetal Subunit of Spongistatin 1 (Altohyrtin A).
Pettit, G. et al., (Mar. 12, 1993), *J. Org. Chem.*, 58(6):1302–1304 "Isolation and Structure of Spongistatin $1^{1a}$".
Uckun, F. et al., (May 15, 1995), *Blood*, 85(10):2817–2828 "In Vitro and In Vivo Activity of Topotecan Against Human B–Lineage Acute Lymphoblastic Leukemia Cells".
Vassilev, A. et al., (Jan. 15, 1999), *J. Biol Chem.*, 274(3):1646–1656 "Bruton's Tyrosine Kinase as an Inhibitor of the Fas/CD95 Death–inducing Signaling Complex".

(List continued on next page.)

Primary Examiner—Deborah C. Lambkin
(74) Attorney, Agent, or Firm—Merchant & Gould P.C.

(57) ABSTRACT

Novel tubulin binding compounds (SPIKETS) having potent tubulin depolymerization activity and inhibitory activity against tubulin polymerization. The compounds are effective agents for inhibiting cellular proliferation, for example, in cancer cells. The compounds are adapted to interact favorably with a novel SP binding pocket on tubulin, which pocket is useful for screening of anti-tubulin, anti-proliferation, and anti-cancer drugs.

17 Claims, 11 Drawing Sheets

OTHER PUBLICATIONS

Vig, R. et al., (Oct. 1998), *Bioorganic & Medicinal Chemistry*, 6(10):1789–1797 "Rational Design and Sythesis of Phenethyl–5–bromopyridyl Thiourea Derivatives as Potent Non–Nucleoside Inhibitors of HIV Reverse Transciptase".

Evans, D. et al., "Enantioselective Synthesis of Altohyrtin C(Spongistatin 2): Fragment Assembly and Revision of the Spongistatin 2 Stereochemical Assignment", *Angew Chem. Int. Ed. Engl.*, vol. 36, No. 24, pp. 2744–2747 (1997).

Evans, D. et al., "Enantioselective Synthesis of Altohyrtin C (Spongistatin 2): Synthesis of the AB–and CD–Spiroketal Subunits", *Angew Chem. Int. Ed. Engl.*, vol. 36, No. 24, pp. 2738–2741 (1997).

Guo, J. et al., "Total Synthesis of Altohyrtin A (Spongistatin 1): Part 1", *Angew Chem. Int. Ed.*, vol. 37, No. ½, pp. 187–192 (1998).

Paterson, I. et al., "Studies in Marine Macrolide Synthesis: Stereocontrolled Synthesis of the AB–Spirocetal Subunit of Spongistatin 1 (Altohyrtin A)", *Tetrahydron Letters*, vol. 37, No. 47, pp. 8581–8584 (1996).

Paterson, I. et al., "Studies in Marine Macrolide Synthesis: Synthesis of a Fully Functionalised $C_1$–$C_{28}$ Subunit of Spongistatin 1 (Altohyrtin A)", *Tetrahydron Letters 39*, pp. 8545–8548 (1998).

Paterson, I. et al., "Studies in Marine Macrolide Synthesis: Synthesis of the $C_1$–$C_{15}$ Subunit of Spongistatin 1 (Altohyrtin A) and 15,16–Anti Aldol Coupling Reactions", *Tetrahydron Letters*, vol. 38, No. 47, pp. 8241–8244 (1997).

Paterson, I. et al., "Studies in Marine Macrolide Synthesis: Synthesis of a $C_{16}$–$C_{28}$ Subunit of Spongistatin 1 (Altohyrtin A) Incorporating the CD–Spiroacetal Moiety", *Tetahedron Letter*, vol. 38, No. 51, pp. 8911–8914 (1997).

Smith, III, A. et al., "Spongistatin Synthetic Studies. 2. Assembly of the C(18–28) Spiroketal", *Tetrahydron Letters*, vol. 38, No. 50, pp. 8671–8674 (1997).

Smith, III, A. et al., "Spongistatin Synthetic Studies. 3. Construction of the C(1–17) Spiroketal", *Tetrahydron Letters*, vol. 38, No. 50, pp. 8675–8678 (1997).

Terauchi, T. et al., "Synthetic Studies on Altohyrtins (Spongistatins): Synthesis of the C1–C14 (AB) Spiroacetal Portion", *Tetrahydron Letters 39*, pp. 3795–3798 (1998).

Avila, J., "Microtubule Functions", *Life Sci.*, vol. 50, No. 5, pp. 327–334 (1992).

Bai, R. et al., "Spongistatin 1, A Highly Cytotoxic, Sponge–Derived, Marine Natural Product That Inhibits Mitosis Microtubule Assembly, And The Binding Of Vinblastine To Tubulin", *Molecular Pharmacology*, vol. 44, No. 4, pp. 757–766 (Oct. 1993).

Bai, R. et al., "The Spongistatins, Potently Cytotoxic Inhibitors Of Tubulin Polymerization, Bind In A Distinct Region Of The Vinca Domain", *Biochemistry*, vol. 34, No. 30, pp. 9714–9721 (1995).

Böhm, H., "LUDI: Rule–Based Automatic Design Of New Substituents For Enzyme Inhibitor Leads", *J. Comput.–Aided. Mol. Des.*, vol. 6, pp. 593–606 (Dec. 1992).

Böhm, H., "The Development Of A Simple Empirical Scoring Function To Estimate The Binding Constant For A Protein–Ligand Complex Of Known Three–Dimensional Structure", *J. Comput. Aided. Mol. Des.*, vol. 8, No. 3, pp. 243–256 (Jun. 1994).

Cohen, T. et al., "Synthetically Usefully β–Lithioalkoxides From Reductive Lithiation Of Epoxides By Aromatic Radical Anions", *J. Org. Chem.*, vol. 55, No. 5, pp. 1528–1536 (Mar. 2, 1990).

Connolly, M., "Solvent–Accessible Surfaces Of Proteins And Nucleic Acids", *Science*, vol. 221, No. 4612, pp. 709–713 (Aug. 19, 1983).

Corey, E. et al., "Protection Of Hydroxyl Groups As tert––Butyldimethylsilyl Derivatives", *J. Am. Chem. Soc.*, vol. 94, No. 17, pp. 6190–6191 (Aug. 23, 1972).

Danishefsky, S. et al., "The Total Synthesis Of The Aglycon Of Avermectin $A_{1a}$", *J. Am. Chem. Soc.*, vol. 109, No. 26, pp. 8117–8119 (Dec. 1987).

Downing, K. et al., "Tubulin and Microtubule Structure", *Curr. Opin. Cell. Biol.*, vol 10, No. 1, pp. 16–22 (Feb. 1998).

Hyman, A. et al., "The Role Of Nucleation In Patterning Microtubule Networks", *J. Cell. Sci.*, vol. 111, (15), pp. 2077–2083 (Aug. 1998).

Kozielski, F. et al., "A Model Of The Microtubule–Kinesin Complex Based On Electron Cryomicroscopy And X–ray Crystallography", *Curr. Biol.*, vol. 8, No. 4, pp. 191–198 (Feb. 12, 1998).

Luty, B. et al., "A Molecular Mechanics/Grid Method For Evaluation Of Ligand—Receptor Interactions", *J. Comp. Chem.*, vol. 16, No. 4, pp. 455–464 (Apr. 1995).

Mao, C. et al., "Structure–Based Design Of N–[2–(1–Piperidinylethyl)]N'–[2–(5–Bromopyridyl)]–Thiourea and N–[2–(1–Piperazinylethyl)]N'–[2–(5–Bromopyridyl)]–Thiourea As Potent Non–Nucleoside Inhibitors Of HIV–1 Reverse Transcriptase", *Bioorganic & Medicinal Chemistry Letters*, vol. 8, pp. 2213–2218 (1998).

Nicholls, A. et al., "Protein Folding And Association: Insights From The Interfacial And Thermodynamic Properties Of Hydrocarbons", *Proteins: Structure, Function, and Genetics*, vol. 11, pp. 281–296 (1991).

Nogales, E. et al., "High–Resolution Model Of The Microtubule", *Cell*, vol. 96, No. 1, pp. 79–88 (Jan. 8, 1999).

Nogales, E. et al., "Structure Of the αβ Tubulin Dimer By Electron Crystallography", *Nature*, vol. 391, No. 6663, pp. 199–202 (Jan. 8, 1998).

Pettit, G. et al., "Isolation and Structure Of Spongistatin $1^{1a}$", *J. Org. Chem.*, vol. 58, No. 6, pp. 1302–1304 (Mar. 12, 1993).

Uckun, F. et al., "In Vitro and In Vivo Activity Of Topotecan Against Human B–Lineage Acute Lymphoblastic Leukemia Cells", *Blood*, vol. 85, No. 10, pp. 2817–2828 (May 15, 1995).

Vassilev, A. et al., "Bruton's Tyrosine Kinase Kinase As An Inhibitor Of The Fas/CD95 Death–Inducing Signaling Complex", *J. Biol. Chem.*, vol. 274, No. 3, pp. 1646–1656 (Jan. 15, 1999).

Vig, R. et al., "Rational Design And Synthesis of Phenethyl–5–Bromopyridyl Thiorea Derivatives As Potent Non–Nucleoside Inhibitors Of HIV Reverse Transcriptase", *Bioorganic & Medicinal Chemistry*, vol. 6, No. 10, pp. 1789–1797 (Oct. 1998).

* cited by examiner

Structure of Spongistatin (SP) and SPIKET-P1

SPIKET-P1

SYNTHETIC SPIROKETAL PYRANES AS POTENT ANTI-CANCER AGENTS

Provisional Application No. 60/091,002 filed on Jun. 29, 1998.

FIELD OF THE INVENTION

The invention relates to novel tubulin depolymerization agents, SPIKET, as potent anti-cancer agents.

BACKGROUND OF THE INVENTION

Cancer is a major disease that continues as one of the leading causes of death at any age. In the United States alone, it is anticipated that more than a half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

Cellular proliferation, for example, in cancer and other cell proliferative disorders, occurs as a result of cell division, or mitosis. Microtubules play a pivotal role in mitotic spindle assembly and cell division[1-5]. These cytoskeletal elements are formed by the self-association of the αβ tubulin heterodimers[1-5]. Agents which induce depolymerization of tubulin and/or inhibit the polymerization of tubulin provide a therapeutic approach to the treatment of cell proliferation disorders such as cancer.

Recently, the structure of the αβ tubulin dimer was resolved by electron crystallography of zinc-induced tubulin sheets[6]. According to the reported atomic model, each 46×40×65 Å tubulin monomer is made up of a 205 amino acid N-terminal GTP/GDP binding domain with a Rossman fold topology typical for nucleotide-binding proteins, a 180 amino acid intermediate domain comprised of a mixed β sheet and five helices which contain the taxol binding site, and a predominantly helical C-terminal domain implicated in binding of microtubule-associated protein (MAP) and motor proteins[2, 5].

Novel tubulin-binding molecules which, upon binding to tubulin, interfere with tubulin polymerization, can provide novel agents for the inhibition of cellular proliferation and treatment of cancer.

Spongistatin (SP) (FIG. 1) is a potent tubulin depolymerizing natural product isolated from an Eastern Indian Ocean sponge in the genus Spongia[7]. Spongistatins are 32-membered macrocyclic lactone compounds with a spongipyran ring system containing 4 pyran-type rings incorporated into two spiro[5.5]ketal moieties[7]. In cytotoxicity assays, spongistatin (SP) exhibited potent cytotoxicity with subnanomolar $IC_{50}$ values against an NCI panel of 60 human cancer cell lines[7]. SP was found to inhibit the binding of vinc alkaloids (but not colchicin) to tubulin[8], indicating that the binding site for this potent tubulin depolymerizing agent may also serve as a binding region for vinc alkaloids.

Novel tubulin binding compounds, which upon binding to tubulin, interfere with tubulin assembly, for example by causing depolymerization of tubulin or by inhibiting tubulin polymerization, would provide novel agents for the prevention of cellular proliferation, for example in the inhibition of tumor cell growth and treatment of cancer.

SUMMARY OF THE INVENTION

A novel binding pocket has been identified in tubulin, which binding pocket accepts and binds novel, small molecule tubulin binding spiroketal pyrane compounds of the invention. Binding of the spiroketal pyranes (SPIKETs) to tubulin causes tubulin depolymerization, and/or inhibits tubulin polymerization. The siroketal pyranes of the invention are therapeutically effective as cytotoxic agents, to inhibit cellular proliferation, and as effective anti-cancer agents.

The compounds of the invention have the general structure shown in formula I, and are designed to include moieties and/or substitutions capable of favorable interaction with amino acid residues in the SPIKET binding pocket of tubulin. For example, $R^1$, $R^2$, $S^1$, and $S^2$ preferably contain functional groups and/or substitutions designed to favor hydrophobic interaction and/or Van der Waals interaction with hydrophobic residues of the SPIKET binding pocket, as described more fully below.

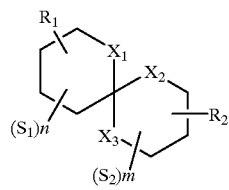

(I)

wherein $X^1$, $X^2$, and $X^3$ are the same or different, and are each independently O, C, or S;

$R^1$ and $R^2$ are the same or different and are each independently H, provided both $R^1$ and $R^2$ are not H, or $(C_1-C_8)$alkyl, $(C_1-C_8)$cycloalkyl, $(C_1-C_8)$alkoxy, $(C_1-C_8)$aryloxy, $(C_1-C_8)$arylthio, $(C_1-C_8)$aryl, $(C_1-C_8)$heteroaryl, $C(=)NR^aR^b$ or $NR^aR^b$; wherein $R^a$ and $R^b$ are each independently hydrogen, acyl, $(C_1-C_8)$alkyl, $(C_3-C_7)$cycloalkyl, $(C_6-C_{10})$aryl, or $(C_6-C_{10})$heteroaryl, or $R_a$ and $R_b$ together with the nitrogen to which they are attached form a ring such as pyrrolidino, piperidino, morpholino, or thiomorpholino;

n and m are the same or different, and are each independently 0 to 7;

$S_1$ and $S^2$ can be the same or different, and are each independently OH, SH, $CO_2H$, halogen, CN, acyl, thioacyl, ester, thioester, $(C_1-C_6)$alkoxy, $(C_1-C_6)$aryloxy, $(C_1-C_6)$alkylthio, $(C_1-C_6)$arylthio, $(C_1-C_6)$alkyl, $(C_1-C_6)$alkenyl, $(C_1-C_6)$alkynyl, $(C_3-C_7)$cycloalkyl, $(C_6-C_{10})$aryl, or $(C_6-C_{10})$heteroaryl, $C(=O)NR^aR^b$ or $NR^aR^b$; wherein $R^a$ and $R^b$ are each independently hydrogen, acyl, $(C_1-C_6)$alkyl, $(C_3-C_7)$cycloalkyl, $(C_6-C_{10})$aryl, or $(C_6-C_{10})$heteroaryl, or $R^a$ and $R^b$ together with the nitrogen to which they are attached form a ring such as pyrrolidino, piperidino, morpholino, or thiomorpholino;

taken together, any two $S^1$ and $S^2$ can form a ring, and any two adjacent substituents can form a double bond between the two carbons to which they are attached. The hydrocarbon moieties of $R^1$, $R^2$, $S^1$, and $S^2$ may be substituted or unsubstituted.

Particular embodiments of the claimed compounds, for example, those compounds depicted in formulae II–V and preferred compounds of the invention are described below in the Detailed Description, Examples, and Claims. Particularly preferred compounds of the invention are:

[(2R,8R)-8-(hydroxymethyl)-1,7-dioxaspiro[5,5]undec-2-yl]methan-1-ol(SPIKET-P1);

Benzyl-protected SPIKET-P1 (SPIKET-P1-P); and 1,13-dibenzyloxy-5,9-dihydroxy-spiroketal (NP25).

The compounds of the invention are combined with a suitable carrier to form compositions suitable for use in binding tubulin, inducing depolymerization of tubulin, inhibiting proliferation of cells, and in the treatment of cancer.

The SPIKET binding pocket on tubulin is useful for designing and screening tubulin binding molecules, anti-cell proliferation agents, and cancer therapeutic agents. Useful agents are designed to fit the pocket and to favorably interact with the pocket for enhanced binding and anti-tubulin activity.

Additional embodiments of the invention are described more fully below.

DETAILED DESCRIPTION OF THE INVENTION

Definitions

Figure 1:
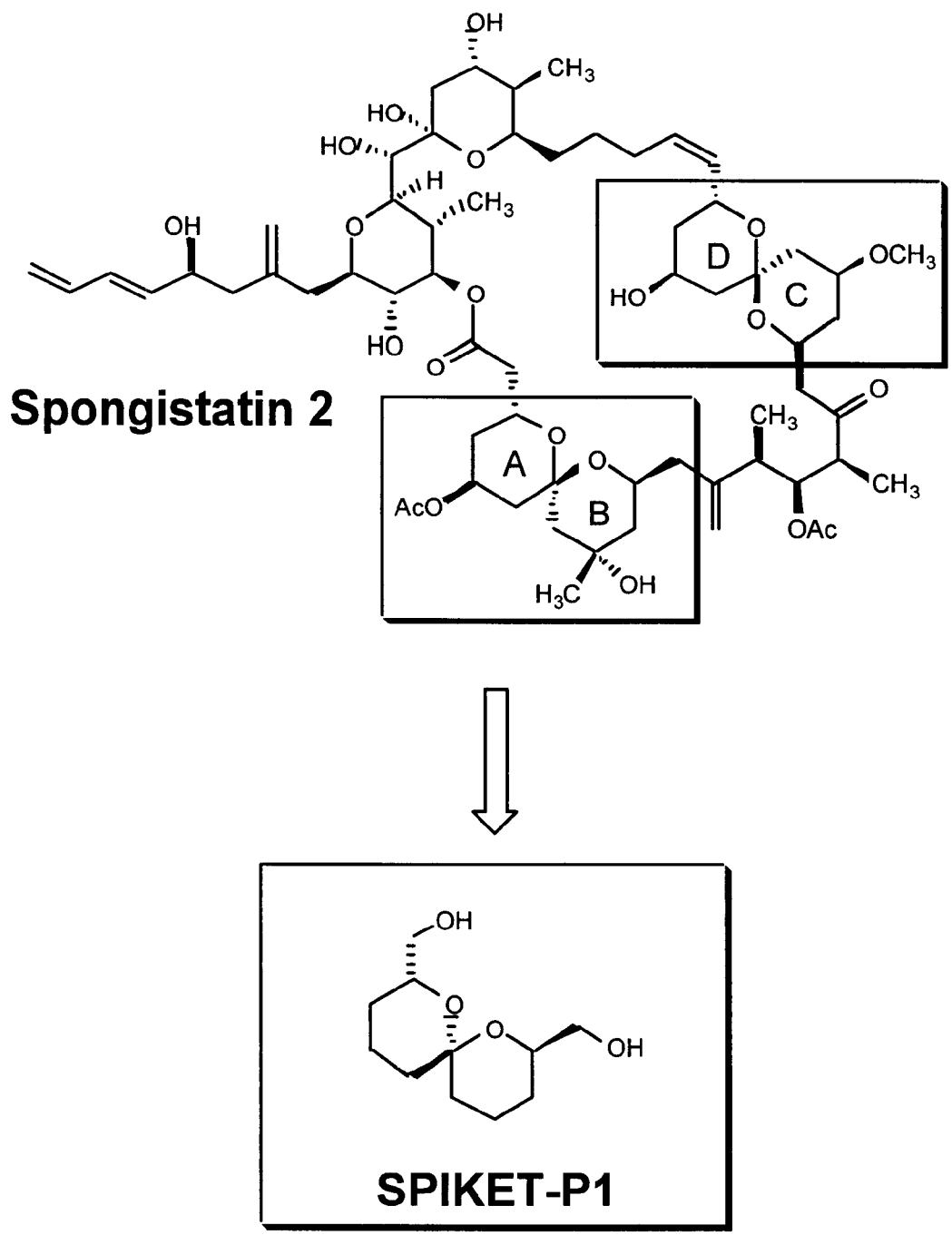
FIG. 1 is a diagram showing the structure of spongistatin (SP) and of SPIKET-P1.

All scientific and technical terms used in this application have meanings commonly used in the art unless otherwise specified. As used in this application, the following words or phrases have the meanings specified.

As used herein, "alkyl", includes both branched and straight-chain saturated aliphatic hydrocarbon groups having the specified number of carbon atoms. As a preferred embodiment, chains of 1 to 22 carbon atoms are included.

As used herein, "alkene", includes both branched and straight chain aliphatic hydrocarbon groups that have at least one double bond.

As used herein, "alkoxy", includes, saturated and unsaturated, branched and straight chain aliphatic hydrocarbon groups having a specified number of carbon atoms where at least one carbon atom forms a single-bond to an oxygen atom.

As used herein "amine", includes primary, secondary, and tertiary amines.

As used herein "halogen" or "halo" substituent includes fluoro, chloro, bromo, and iodo.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

"Substituted cycloalkyl" includes cyclic hydrocarbons having substituents including halo, alkyl, alkenyl, oxyalkyl, oxyalkenyl, haloalkyl, haloalkenyl, and aryl.

"Substituted cycloalkenyl" includes cyclic hydrocarbons having at least one double bond where substituents include halo, alky, alkenyl, oxyalkyl, oxyalkenyl, haloalkyl, haloalkenyl, and aryl.

"Substituted aryl" includes aromatic hydrocarbons having substituents including hydroxyl, amino, aminomethyl, halo, alkyl, alkenyl, oxyalkyl, oxyalkenyl, haloalkyl, haloalkenyl, and aryl.

"Treating" or "Treatment" in the context of this invention means the prevention or reduction in severity of symptoms or effects of a pathological condition, including prolonging life expectancy. In the context of cancer therapy, treatment includes prevention of tumor growth, reduction of tumor size, enhanced tumor cell death, and increased apoptosis.

SPIKET Binding Pocket on Tubulin

The binding pocket determined for spongistatin located near the GDP binding site on the surface of tubulin has dimensions of approximately 8 Å wide×18 Å long×11 Å deep. The binding pocket is lined with an unusual cluster of aromatic residues situated in close proximity to each other, including Y108, W103, Y185, W407, Y408, F399, F404, F395, F418, and H406 (See FIG. 2B). The synthetic spiroketal pyrans (SPIKET-P) compounds of the invention, when bound to the tubulin pocket, have the spiroketal ring sandwiched between aromatic residues F404 and W407, providing favorable hydrophobic interactions and van der Waals contacts with these residues (See FIG. 3). Unoccupied volume surrounding the SPIKET-P1 molecule in the binding pocket in the vicinity of the aromatic residues with some hydrophillic residues also nearby, provide a basis for modification of the SPIKET-P molecules to design more potent tubulin binding compounds, and more potent inhibitors of tubulin assembly.

Compounds of the invention are designed to interact favorably with the binding pocket. In particular, the aromatic ring substituents on the SPIKET-P compounds provide favorable contacts with aromatic residues such as F399, Y408, Y185, and H406. Hydrophilic substituents added to the ring offer hydrogen binding capability with hydrophilic residues such as H406, K105, E411, and N101. (see, FIG. 3).

The invention thus includes compounds designed to interact favorably with the binding pocket, methods for designing and screening such compounds, and methods for screening useful tubulin inhibitors and anti-cancer therapeutic agents.

Compounds of the Invention

In general, the compounds of the invention include those having spiroketal subunits suitable for binding to the spongistatin binding pocket of tubulin. Compounds of the invention include those having the following structural formula:

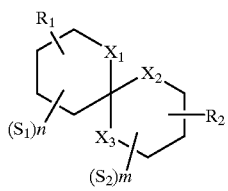

(I)

wherein
  $X^1$, $X^2$, and $X^3$ are the same or different, and are each independently O, C, or S;
  $R^1$ and $R^2$ are the same or different and are each independently H, provided both $R_1$ and $R^2$ are not H, or $(C_1-C_8)$alkyl, $(C_1-C_8)$cycloalkyl, $(C_1-C_8)$alkoxy, $(C_1-C_8)$aryloxy, $(C_1-C_8)$arylthio, $(C_1-C_8)$aryl, $(C_1-C_8)$heteroaryl, $C(=)NR^aR^b$ or $NR^aR^b$; wherein $R^a$ and $R^b$ are each independently hydrogen, acyl, $(C_1-C_8)$ alkyl, $(C_3-C_7)$cycloalkyl, $(C_6-C_{10})$aryl, or $(C_6-C_{10})$ heteroaryl, or $R_a$ and $R_b$ together with the nitrogen to which they are attached form a ring such as pyrrolidino, piperidino, morpholino, or thiomorpholino;
  n and m are the same or different, and are each independently 0 to 7; $S^1$ and $S^2$ can be the same or different, and are each independently OH, SH, $CO_2H$, halogen, CN, acyl, thioacyl, ester, thioester, $(C_1-C_6)$alkoxy, $(C_1-C_6)$aryloxy, $(C_1-C_6)$alkylthio, $(C_1-C_6)$arylthio, $(C_1-C_6)$ alkyl, $(C_1-C_6)$alkenyl, $(C_1-C_6)$alkynyl, $(C_3-C_7)$ cycloalkyl, $(C_6-C_{10})$aryl, or $(C_6-C_{10})$heteroaryl, $C(=O)NR^aR^b$ or $NR^aR^b$; wherein $R^a$ and $R^b$ are each independently hydrogen, acyl, $(C_1-C_6)$alkyl, $(C_3-C_7)$ cycloalkyl, $(C_6-C_{10})$aryl, or $(C_6-C_{10})$heteroaryl, or $R^a$ and $R^b$ together with the nitrogen to which they are attached form a ring such as pyrrolidino, piperidino, morpholino, or thiomorpholino; taken together, any two $S^1$ and $S^2$ can form a ring, and any two adjacent substituents can form a double bond between the two carbons to which they are attached. The hydrocarbon moieties of $R^1$, $R^2$, $S^1$, and $S^2$ may be substituted or unsubstituted.

Alternative embodiments of the invention include those compounds having the structures of formulae II–VI:

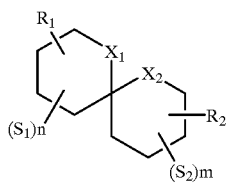

(II)

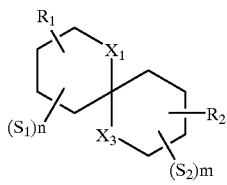

(III)

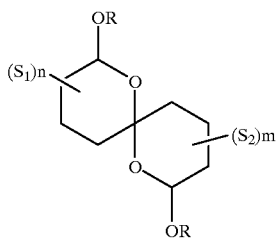

(IV)

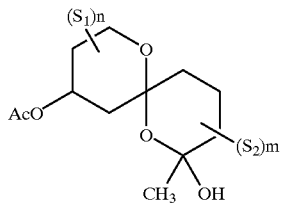

(V)

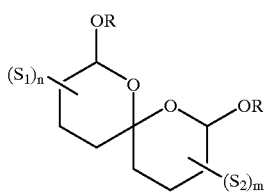

(VI)

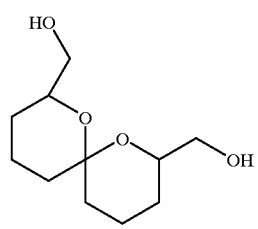

The spiroketal ring substituents and substitutions are of a size and chemical functionality so as to permit favorable interaction with the SP binding pocket of tubulin. Preferred compounds of the invention are shown in the data tables provided in the Examples below, and include the following compounds:

S-P1

S-P1-P

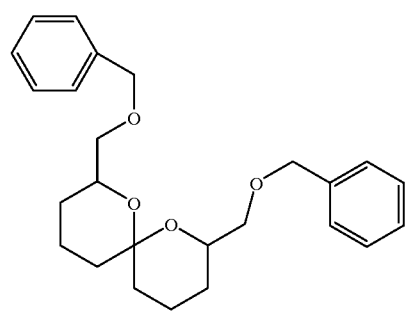

-continued

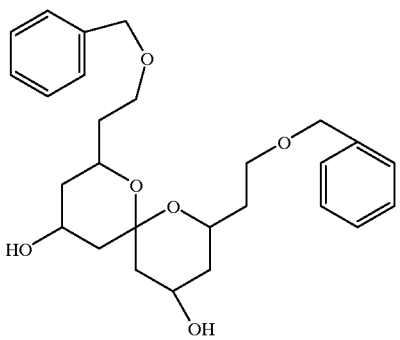

NP-25

Using the modeling and docking data provided in the Description and Examples, one of skill in the art can modify the spiroketal pyran compounds of the invention to promote binding to tubulin and to produce active therapeutic agents. Some such modifications and agents are shown in the synthetic libraries provided in the Examples.

Salts

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention. As used herein, the compounds of the invention inlcude their salts.

Depolymerization of Tubulin

The compounds of the invention bind to tubulin at a unique, novel binding pocket of tubulin. Upon binding the tubulin binding compounds, tubulin is caused to depolymerize and/or inhibitition of tubulin assembly results. Suitable assays for the antitubulin acitivity of the inventive compounds are disclosed in the Examples below.

Tumor Treatment

The compounds of the invention can be used in methods of tumor treatment, for example, by administering to a subject a compound of the invention in order to achieve an inhibition of tumor cell tubulin assembly and/or depolymerization of tumor cell tubulin, inhibition of tumor cell growth, a killing of tumor cells, induced apoptosis, and/or increased patient survival time.

The anti-cancer tubulin binding compounds of the invention are suitable for use in mammals. As used herein, "mammals" means any class of higher vertebrates that nourish their young with milk secreted by mammary glands, including, for example, humans, rabbits, and monkeys.

Administration Methods

The compounds of the present invention can be formulated as pharmaceutical compositions and administered to a mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleageneous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

Useful Dose

When used in vivo to kill or inhibit the growth of tumor cells, the administered dose is that effective to have the desired effect, such as is sufficient to reduce or eliminate tumors. Appropriate amounts can be determined by those skilled in the art, extrapolating using known methods and relationships, from the in vitro data provided in the Examples.

In general, the dose of the novel tubulin binding compounds effective to achieve tumor cell apoptosis, reduction in tumors, and increased survival time, is 1–100 mg/kg body weight/dose for a direct targeted administration. The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the tubulin binding compounds may be less than for single drug therapy.

EXAMPLES

The invention may be further clarified by reference to the following Examples, which serve to exemplify some of the embodiments, and not to limit the invention in any way.

METHODS

Chemistry.

Unless stated otherwise, all chemicals were purchased from Aldrich (Milwaukee, Wis.) and were used without further purification. Unless otherwise noted, each reaction vessel was secured with a rubber septa, and the reaction was performed under nitrogen atmosphere. $^1$H and $^{13}$C NMR spectra were obtained on a Varian Mercury 300 instrument at ambient temperature in the solvent specified. Melting points were determined using a Fisher-Johns melting point apparatus and are uncorrected. FT-IR spectra were recorded on a Nicolet Protege 460 spectrometer. GC/MS was obtained on a HP6890 GC System Ar equipped with a HP5973 Mass Selective Detecter. The molecular weights were obtained by GC-MS (HP GC System 6890 Series). Analytical thin-layer chromatography was done on Whatman silica 60 aluminum coated plates. Flash column chromatography was carried out with 230–400 mesh silica gel.

Example 1

Spongistatin Binding Pocket on Tubulin

In a rational drug design effort intended to determine the minimal molecular architecture of the SP structure necessary for biologic activity, we used the 3-D atomic model of the αβ tubulin dimer for the identification of the potential tubulin binding sites for SP. Our integrated effort to identify the SP binding site involved "cavity searching", analysis of the binding environment, docking procedures based on the electron crystallographic coordinates of tubulin, and the calculation of the binding constant by a modified score function (LUDI score function).

SP is a macrocyclic molecule with dimensions larger than 10 Å wide and 10 Å long. The large molecular volume of SP may contribute to its remarkable potency as a tubulin depolymerizing agent and suggests that it may bind to a deep pocket on or near the surface of tubulin, providing a highly hydrophobic environment for molecular interactions. We examined the tubulin structure using graphics programs including GRASP (A. Nicholls, GRASP, Graphical Representation and Analysis of Surface Properties, 1992, New York) and INSIGHTII (Molecular Simulations Inc., 1996, San Diego, Calif.) to identify a possible binding site for SP that would have suitable dimensions and contain a cluster of hydrophobic residues near the protein surface.

Figure 2A:
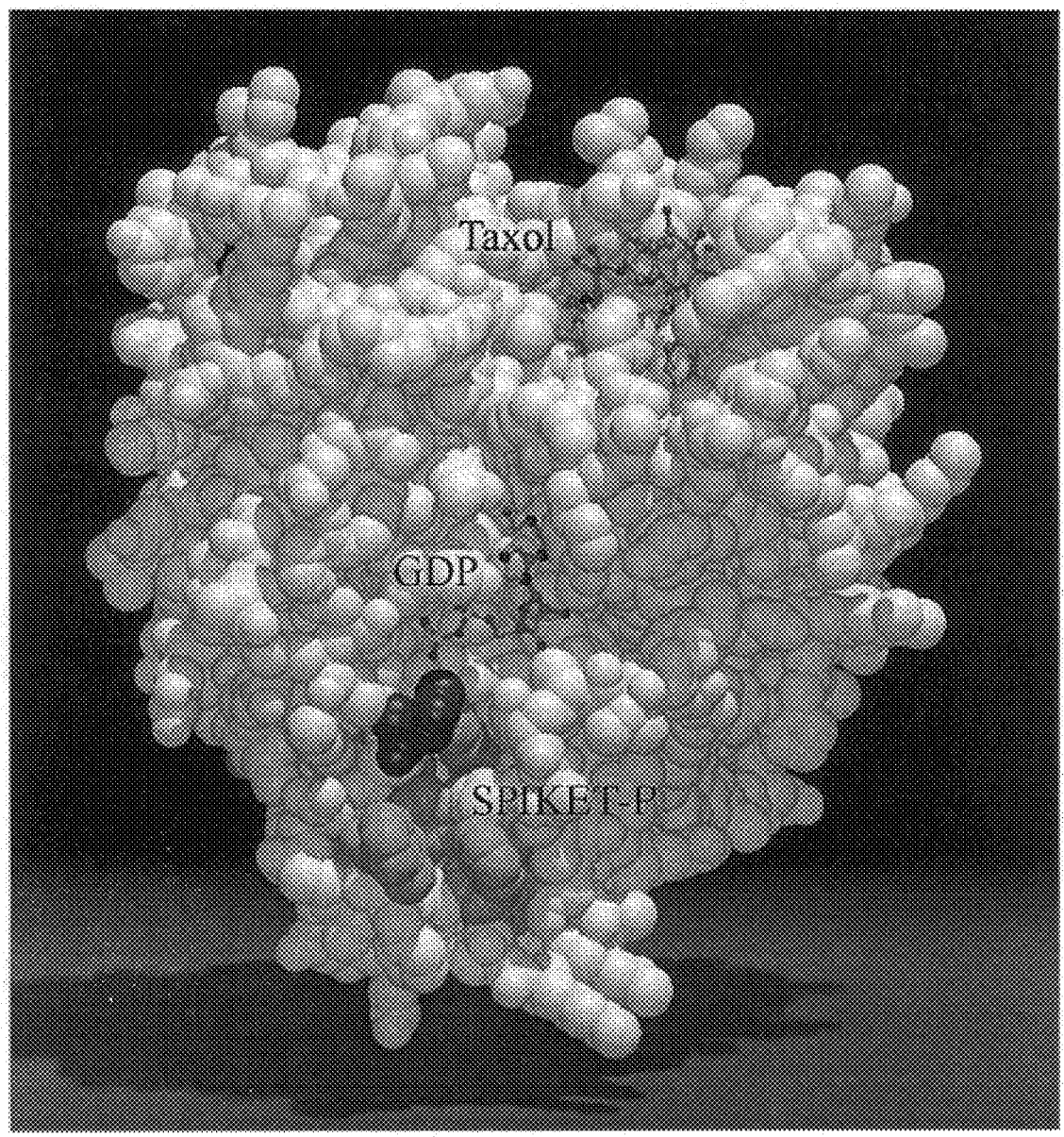
FIG. 2A is a photograph of a space filling model of beta-tubulin, shown with ball and stick models of GDP and Taxoter molecules binding to their respective binding sites as labeled. The spongistatin binding site (SBP) is marked and shown in orange in the color photograph for all aromatic residues in close range. Tubulin residue N101, shown in red, is located near the GDP binding site.
Figure 2B:
FIG. 2B is a ribbon representation of bea-tubulin, shown with an aromatic residue cluster as a remarkable characteristic of the spongistatin binding site.

The search resulted in the discovery of a unique candidate binding pocket on the tubulin surface which is large enough to accommodate SP and can also provide an environment for extensive hydrophobic interactions. The SP molecule was then docked into this candidate binding site using the Affinity module within the Insight II program (Molecular Simulations Inc., 1996, San Diego, Calif.). The initial coordinates of SP, representing several different conformations, were modeled and energy-minimized using the DISCOVER program (Biosym Technologies Inc., San Diego, Calif.). The docking results which utilized different conformations of SP were analyzed and ranked based on their interaction scores, as shown in the examples below. The SP model which was assigned the highest interaction score and lowest potential energy was chosen for further calculations. The docking simulation results indicated that the putative SP binding pocket located on the surface of tubulin is approximately 8 Å wide×18 Å long×11 Å deep (FIG. 2A). The pocket consists of an unusual cluster of aromatic residues situated in close proximity including Y108, W103, Y185, W407, Y408, F399, F404, F395, F418, and H406 (FIG. 2B).

The proposed tubulin binding site for SP is in close proximity to the GDP exchange site on the β subunit of the tubulin heterodimer (FIG. 2). This location for the SP binding site would provide a cogent explanation for the ability of SP to inhibit the displacement of the bound GDP molecules from tubulin[8, 9]. Furthermore, according to the recently published high-resolution model of the microtubule structure[10], this binding pocket contacts the longitudinal interdimer interface of the microtubule; the existence of bound SP in this binding pocket may therefore hinder interdimer interactions of tubulin and contribute to the tubulin depolymerizing activity of SP. Advanced modeling studies of the interactions of SP with this putative SP binding pocket indicated that the two spiroketal groups of SP are in close contact with protein residues lining the binding pocket and may therefore serve as the critical binding components of SP.

Figure 3:
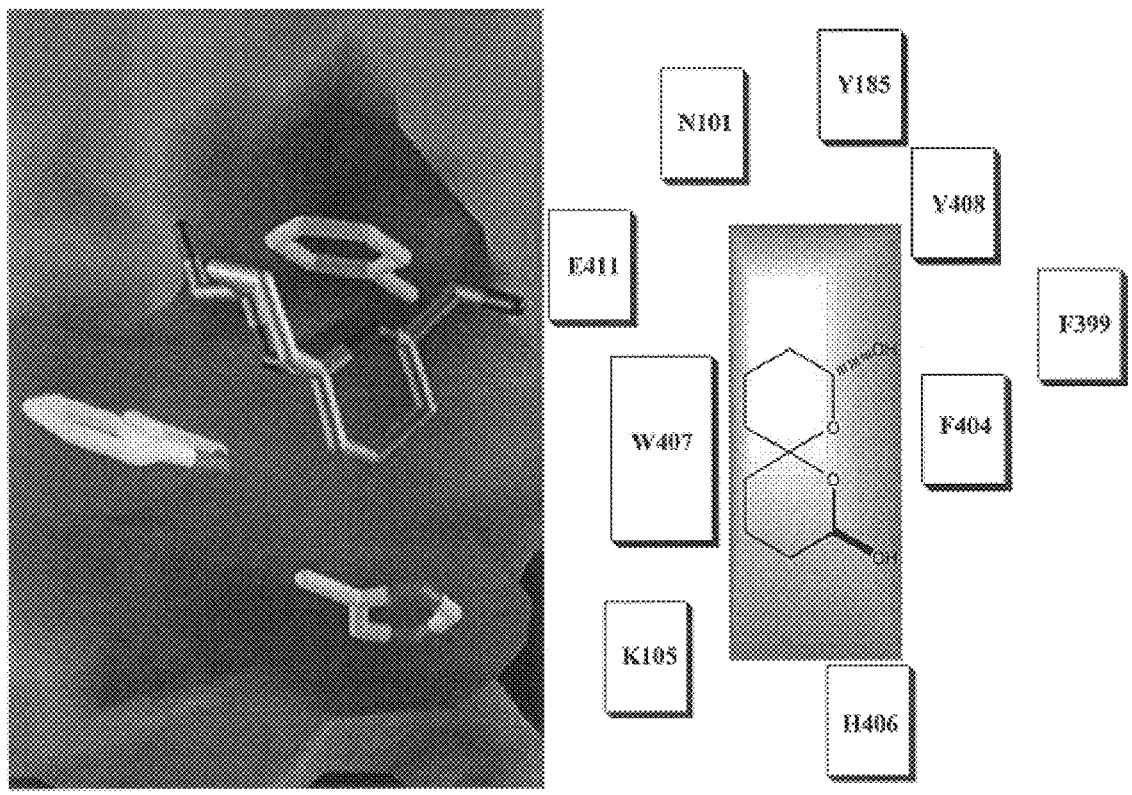
FIG. 3 is a schematic representation of SPIKET-P1 docked in its binding site in tubulin. Shown are the tubulin residues available for interaction with SPIKET-P1.

The identification of the spiroketal subunits as the likely tubulin binding elements of SP prompted the hypothesis that simple synthetic spiroketal pyrans ("SPIKET-P compounds") representing these subunits, such as compound SPIKET-P1 (FIG. 3), could serve as SP pharnacophores. Docking studies indicated that, when bound to tubulin, the spiroketal ring of SPIKET-P1 would be sandwiched between aromatic residues F404 and W407 in the binding pocket and would provide favorable hydrophobic interactions and van der Waals contacts with these residues (FIG. 3). Moreover, an analysis of the SPIKET-P1 binding environment indicated some unoccupied volume surrounding the docked SPIKET-P1 molecule (see FIG. 3) in the vicinity of mostly hydrophobic aromatic residues mixed with a few hydrophilic residues.

Unlike hydrogen bonding interactions, hydrophobic interactions between a protein and a bound inhibitor are relatively insensitive to the precise positioning and orientation of the functional groups involved in the interactions. Therefore, we reasoned that the best strategy for increasing favorable molecular interactions between tubulin and a spiroketal pyran inhibitor would be to survey the effect of adding different functional groups on the inhibitor. This was accomplished by using a combinatorial chemistry approach in combination with structure-based design procedures to develop more potent derivatives of SPIKET-P1. Specifically, our computer-generated binding pocket model of tubulin was used to define favorable interaction regions in the binding site which dictate preferred substituents on SPIKET-P1.

The selection of substituents also takes into consideration the ease of chemical synthesis and takes full advantage of a high-throughput assay to identify the most active tubulin-depolymerizing derivatives. Using this approach, we devised a combinatorial library of aromatic substituents combined with hydrophilic groups on the ring for SPIKET-P1 as our first-generation designs of tubulin-depolymerizing agents which were identified based on the defined size of the tubulin binding pocket and the existence of several aromatic residues surrounding the predicted binding position of the parent compound, SPIKET-P1. The aromatic ring substituents on the inhibitor would provide favorable contacts with aromatic residues lining the tubulin binding site (residues F399, Y408, Y185 and H406) whereas hydrophilic substituents added to the ring would offer opportunities for hydrogen bonding with hydrophilic residues that are slightly more distant (residues H406, K105, E411 and N101 (FIG. 3)).

SPIKET-P1 interaction with the tubulin SP binding site is illustrated in a surface model of the SP binding site and stick-and-ball model for SPIKET-P1 molecule. The spiroketal ring is sandwiched between phenylalanine 404 and tryptophan 407 (shown in the color photograph of FIG. 3 in light blue and magenta) and close to a histidine (colored in green).

The Spiroketal ring of the SPIKET-P1 is in close contact with the surrounding hydrophobic residues with 75% of 218 Å$^2$ total molecular surface buried. The calculation and figure was prepared using GRASP[11] There is no hydrogen bonding observed between SPIKET-P1 and protein residues. Two hydroxyl groups on SPIKET-P1 point toward unoccupied pockets which have room for larger substituents on SPIKET-P1. The inspection of SPIKET-P1 aromatic-residue-rich environment indicates that substitution of the hydroxyl groups by hydrophobic rings would provide more favorable interactions with surrounding aromatic residues.

The spiroketal group of SPIKET-P1 has a molecular surface of 218 Å$^2$, 75% of which would be covered by the aforementioned two aromatic rings. Therefore, SPIKET-P1 (FIG. 3) was selected as our first synthetic target. Retrosynthetic analysis of SPIKET-P1 (Scheme 1) shown in Example 2 below, indicated that SPIKET-P1 could be prepared using a versatile multi-step synthetic scheme in a stereocontrolled fashion.

Initially, the binding position was determined based on the position of the A-B spiroketal group of spongistatin in SP binding site. The coordinates of SPIKET-P1 used in the following docking procedure were taken from the X-ray crystal structure (Example 3, FIG. 4). Then SPIKET-P1-P and NP-25 were built on the SPIKET-P1 coordinates using the Sketcher module in the InsightII program (Molecular Simulation Inc., 1996, San Diego, Calif.). Fixed docking in the Affinity module within InsightII was used for docking small molecules to the binding site of tubulin which was determined from the electron crystal structure and further defined from visual inspection. The docking program has the ability to define a radius of residues within a 7 Å distance from the ligand molecule. As the modeling calculations progressed, the residues within the defined radius were allowed to move in accordance with energy minimization. Ten final target positions were defined for each molecule which had starting positions randomly assigned. The final docked position of the molecule was chosen based on both the lowest energy estimation and the highest score rank which was defined by a modified LUDI function[15, 16] (described below) for the search target. Calculations were carried out on a SGI INIDIGO2 using the CVFF force field in the Discover program and a Monte Carlo search strategy in Affinity[17]. No solvation procedures were used. Since the total number of movable atoms exceeded 200, conjugated gradient minimization was used instead of the Newton minimization method to conserve CPU time.

We imposed several modifications during the calculation of inhibitory constants ($K_i$ values) of the positioned compounds using the Ludi score function[15, 16] and previously used to successfully predict the trend of the experimental data[18,19]. First, the molecular surface areas (MS) were directly calculated from the coordinates of the compounds in docked conformations using the MS program[20]. Second, we re-evaluated the number of rotatable bonds (NR) which was sometimes assessed inaccurately by INSIGHTII (Molecular Simulations Inc., 1996, San Diego, Calif.). The score function that we used is shown below:

Modified Ludi score function=MS×BS×2.93+85×(H-bond#) −NR×24.2−95, Log $K_d$=−Score/100 where NR is the number of rotatable bond; MS is the molecular surface calculated by MS program; BS is the percentage of the surface area in contact with the protein residues; H-bond# is the number of the hydrogen bond; $K_d$ is binding constant. For SPA1 molecular, MS=218 Å$^2$, BS=75%, H-bond#=0, NR=2, Kd=0.50 mM.

Example 2

Synthesis of SPIKET-P1

Retro-Synthetic Analysis of Spiket-P1

To determine an appropriate synthetic scheme for SPIKET-P1, retrosynthetic analysis was initiated. The spiroketal group in SPIKET-P1 was converted to two hydroxy groups and one carbonyl group. In this manner, the compound became a long chain component shown as 1 in Scheme 1. The resulting compound 1 was further converted to two segments 2 and 3. Both 2 and 3 were derived from 4 which was synthesized from the commercially available benzyl (R)-(−)-glycidyl ether 5 in four steps.

Scheme 1:

Retro-Synthetic Analysis of SPIKET-P1

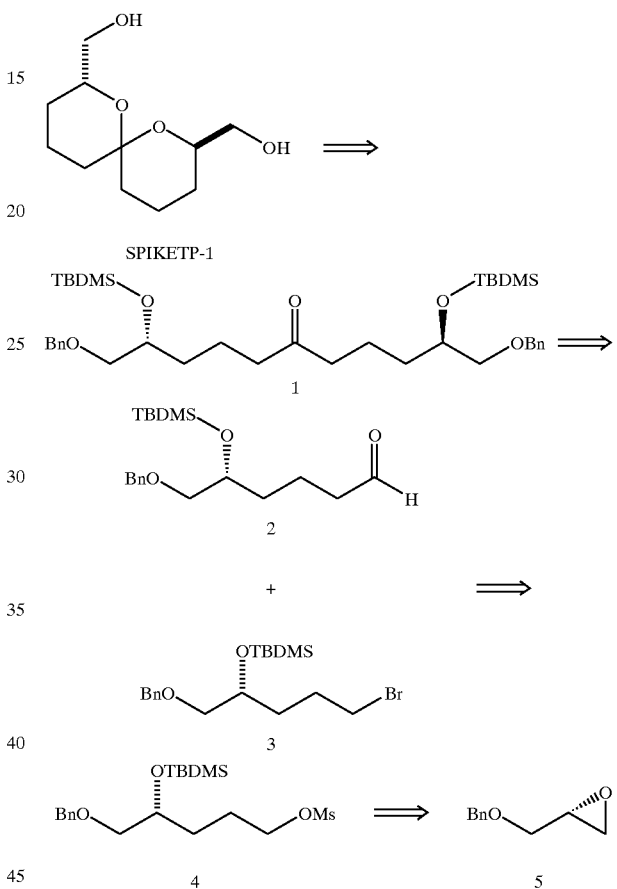

Synthesis of Spiket-P1

An 11-step synthesis of SPIKET-P1 was performed according to Scheme 2:

Scheme 2:

Stereocontrolled Convergent Synthesis of the SP Pharmacophore SPIKET-P1.

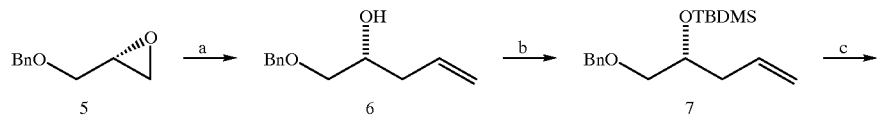

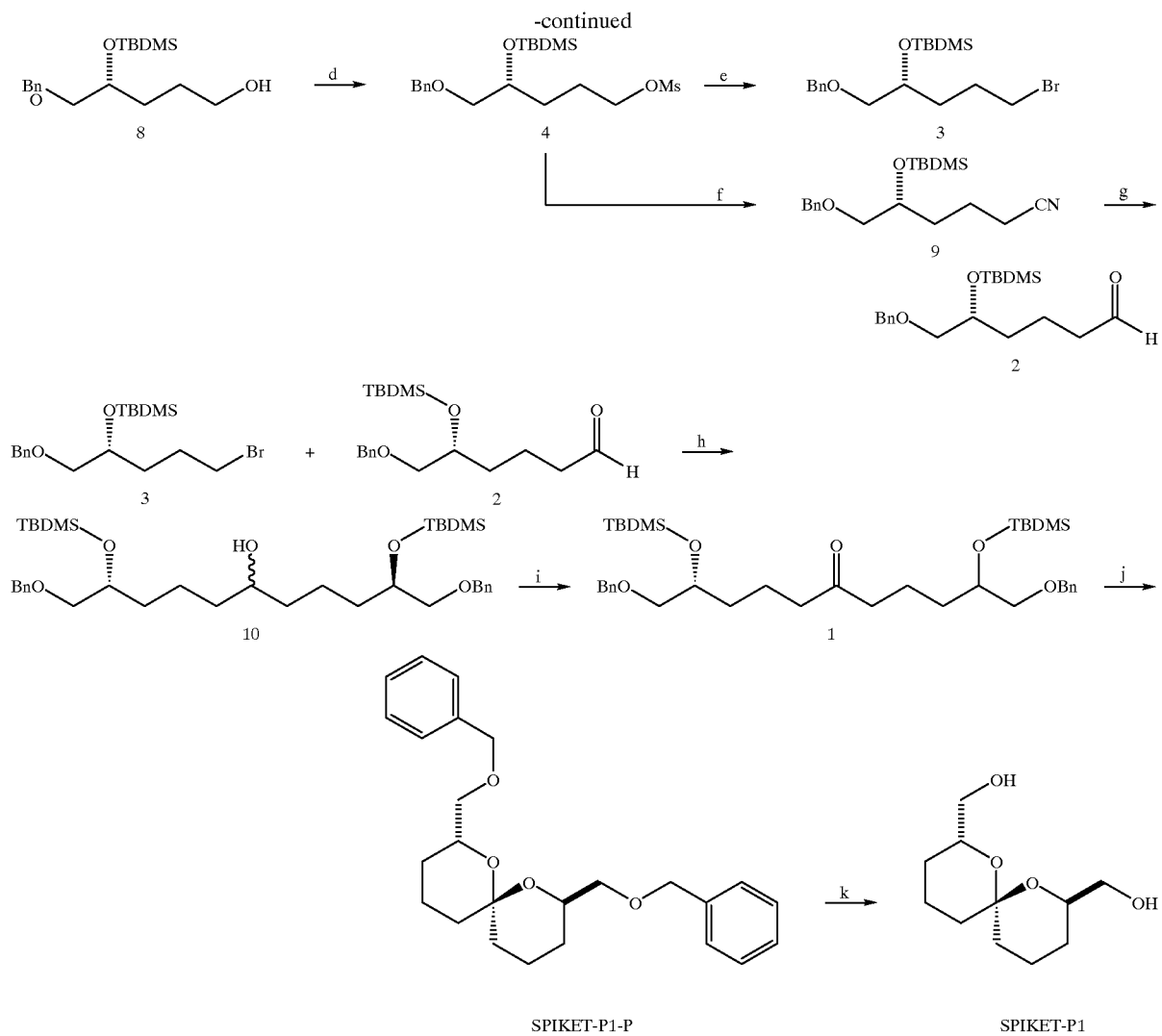

(a) vinylMgBr, CuBr, 2h, 0° C. (b). TBDMSCl, imidazole, DMAP, 1h, 0° C., 3h, rt.
(c) (1), BH$_3$-THF complex, (2), H$_2$O$_2$, NaOH. (d). MsCl, Et$_3$N, 2h, 0° C.
(e). LiBr, Acetone, reflux, 0.5 h. (f). NaCN, DMSO, 15-Crown-5, 40° C., overnight.
(g). DIBAL-H, −78° C. 3h, 10% tartaric acid. (h). Mg/Et$_2$O.
(i). oxalyl chloride, DMSO, Et$_3$N, −78° C. (j). 5% HF/CH$_3$CN, 0.5 h, rt.
(k). LDBB, 0° C.

The synthesis was initiated by opening the commercially available epoxide 5 using vinylmagnesium bromide to obtain the alcohol 6 which was protected as tert-butyldimethylsilyl ether to form 7. Hydroboration of the terminal olefin in 7 yielded the primary alcohol as in 8, which was than converted to the mesylate 4. The mesylate group in 4 was substituted by bromide to form 3. Also the mesylate in 4 was substituted by cyanide to form 9 which was further converted to aldehyde 2 by DIBAL reduction followed by acid catalyzed hydrolysis in one pot reaction. Compound 3 was coupled with 2 by first converting 5 to a Grignard reagent and then reacting it with aldehyde 2 to form 10. Swern oxidation converted 10 to 1. Deprotection of the two tert-butyldimethylsilyl protected hydroxyl groups in 1 followed by acid catalyzed acetal formation to give the immediate benzyl-protected precursor of SPIKET-P1, SPIKET-P1-P. The reaction was carried out in a one pot reaction by treating 1 with 5% HF in acetonitrile at room temperature for 30 minutes. After the unsuccessful attempt of removing the two benzylic protecting groups in SPIKET-P1-P by platinum catalyzed hydrogenation, SPIKET-P1 was obtained by treating SPIKET-P1-P with lithium 4,4'-di-tert-butylbiphenylide (LDBB).

The detailed method for the synthesis of SPIKET-P1 is given below. The step refers to the step given in Scheme 2 above and the name of the step is the name of the resulting product. Characterization data for each intermediate product is also given. The structure of the intermediates can be seen in Scheme 2 above.

(a) 5-Benzyloxy 4R-hydroxy 1-pentene (6). Vinylmagnesium bromide (102.0 mL, 1.0 M in THF) was added to a suspension of CuBr (2.90 g, 10.22 mmol) in anhydrous THF (300 mL) at 0° C. under N$_2$. The benzyl-protected epoxide 5 (8.36 g, 51.00 mmol) in anhydrous THF (20 mL) was then added dropwise. The mixture was stirred at 0° C. for 2 h, then quenched by the addition of saturated NH$_4$Cl, and extracted with EtOAc (3×50 mL), washed with brine, and dried over anhydrous MgSO$_4$. The solvent was removed under reduced pressure. The pure product was obtained by flash column chromatography (Hex/EtOAc=10/1, 7.93 g, 81%): $^1$H NMR (CDCl$_3$) δ 2.27 (m, 2H), 3.37 (dd, J=9.5, 7.0 Hz, 1H), 3.50 (dd, J=9.5, 3.5 Hz, 1H), 3.87 (m, 1H), 4.56 (s, 2H), 5.07 (m, 2H ), 5.82 (m, 1H), 7.32 (m, 5H); $^{13}$C NMR (CDCl$_3$) δ 137.87, 134.15, 128.41, 127.74, 127.69, 117.69, 73.85, 73.35, 69.67, 37.88; GC/MS m/z 192 (M$^+$); IR (neat): 3428, 3071, 3025. 2917, 2860 cm$^{-1}$; [α]$_D^{22}$+4.5 (c 3.3, CH$_3$CO$_2$C$_2$H$_5$).

(b) 5-Benzyloxy 4R-t-butyldimethylsiloxy 1-Pentene (7)$^{21}$. To a well-stirred solution of the olefin 6 (8.23 g, 42.90 mmol) in anhydrous CH$_2$Cl$_2$ (400 mL) at 0° C., anhydrous DMF (40 mL) and imidazole (11.68 g, 171.6 mmol) were added. After the imidazole was dissolved, a catalytic amount of 4-dimethylaminopyridine was added to the mixture, followed by the addition of tert-butyldimethylsilyl chloride (14.23 g, 94.38 mmol). The solution was stirred at 0° C. for 1h and then at room temperature for 2 h. The reaction was quenched with a small amount of water, the two layer separated and the aqueous layer was extracted with ethyl ether (2×100 mL). The combined organic layers were washed with brine, dried over anhydrous MgSO$_4$, and the solvent was removed under reduced pressure. The crude product was purified by flash column chromatography (hexane/ether=10/1) to yield the TBDMS-protected product (12.83 g, 98%): $^1$H NMR (CDCl$_3$) δ 0.05 (s, 6H), 0.88 (s, 9H), 2.25 (m, 1H), 2.33 (m, 1H), 3.38 (d, J=5.7 Hz, 2H), 3.83 (m, 1H), 4.52 (s, 2H), 5.05 (m, 2H), 5.80 (m, 1H), 7.33 (m, 5H); $^{13}$C NMR (CDCl$_3$) δ 138.38, 134.90, 128.25, 127.53, 127.43, 116.97, 74.19, 73.27, 71.15, 39.38, 25.87, 19.19, −4.44, −4.68; IR (neat): 3070, 3027, 2959, 2928, 2857 cm$^{-1}$; [α]$_D^{22}$−3.7 (c 0.5, CH$_3$CO$_2$C$_2$H$_5$).

(c) 5-Benzyloxy 4R-t-butyldimethylsiloxy 1-Pentanol (8). To the solution of olefin 7 (3.03 g, 9.9 mmol) in dry THF (50 mL) was added borane-THF complex (20 mL, 1.0 M solution in THF) at 0° C. under nitrogen and the resulting mixture stirred at rt for 12 h. The reaction was then carefully quenched with water (5.0 mL), then an aqueous solution of NaOH (20 mL, 4.0 N) and 30% H$_2$O$_2$ (20 mL) were added and the reaction mixture was stirred at room temperature for 2 h. The product was extracted with ether (3×80 mL) and the combined organic extracts were washed with brine and dried over anhydrous MgSO$_4$. The solvent was removed under reduced pressure and the residue was purified by flash column chromatography (hexane/ether=4/1 and then hexane: EtOAC=6:1) to provide the desired alcohol (2.26 g, 70%): $^1$H NMR (CDCl$_3$) δ 0.06 (s, 3H), 0.07 (s, 3 H), 0.89 (s, 9H), 1.62 (m, 3H), 1.84 (m, 2H), 3.42 (m, 2H), 3.63 (m, 2H), 3.90 (m, 1H), 4.53 (s, 2H), 7.33 (m, 5H); $^{13}$C NMR (CDCl$_3$) δ 138.23, 128.29, 127.58, 127.51, 74.11, 73.32, 71.04, 63.08, 31.26, 28.23, 25.88, 18.18, −4.77, −4.40; GC/MS m/z 325 (M$^+$+1), 203, 159, 91; IR (neat): 3381, 3070, 3027, 2958, 2927, 2860 cm$^{-1}$; [α]$_D^{22}$+7.5 (c 1.1, CH$_3$CO$_2$C$_2$H$_5$).

(d) 5-Benzyloxy 4R-t-butyldimethylsiloxy 1-pentyl mesylate (4). To a solution of alcohol 8 (3.20 g, 9.90 mmol) in dry CH$_2$C$^2$ (100 mL) was added triethylamine (7.9 mL, 20.68 mmol) and methanesulfonyl chloride (0.86 mL, 10.89 mmol) and the resulting mixture was stirred for 1 hour at 0° C. under N$_2$. The reaction was quenched with water (100 mL) and the product was extracted with CH$_2$Cl$_2$ (3×50 mL). The combined organic layers were washed with brine and dried over MgSO$_4$. The solvent was removed under reduced pressure to provide pure desired product (3.74 g, 94%): $^1$H NMR (CDCl$_3$) δ 0.05 (s, 6H), 0.87 (s, 9H), 1.50–1.90 (m, 4H), 2.99 (s, 3H), 3.34 (dd, J=9.5, 6.0 Hz, 1H), 3.42 (dd, J=9.5, 5.0 Hz, 1H), 3.80 (m, 1H), 4.21 (t, J=6.5 Hz, 2H), 4.51 (s, 2H), 7.33 (m, 5H); $^{13}$C NMR (CDCl$_3$) δ 138.12, 128.32, 127.60, 74.18, 73.33, 70.55, 70.28, 37.38, 30.47, 25.86, 24.93, 18.14, −4.34, −4.77; IR (neat): 3070, 3027, 2929, 2958, 2856 cm$^{-1}$; [α]$_D^{22}$+9.3 (c 1.3, CH$_3$CO$_2$C$_2$H$_5$).

(e) 5-Benzyloxy 4R-t-butyldimethylsiloxy 1-pentyl bromide (3). To mesylate 4 (1.00 g, 2.50 mmol) dissolved in dry acetone (5 mL) was added LiBr (1.09 g, 12.5 mmol). The reaction mixture was refluxed for 0.5 h, and then neutralized with Et$_3$N (5.7 mL, 12.5 mmol). The reaction was quenched by the addition of H$_2$O and the solvent was then removed under reduced pressure. The product was extracted with Et$_2$O (2×50 ml). Flash chromatography gave a pure product (Hexanes/EtOAc=10/1) (0.77 g, 80%): $^1$H NMR (CDCl$_3$) δ 0.04 (s, 3H), 0.05 (s, 3H), 0.88 (s, 9H), 1.57 (m, 1H), 1.71 (m, 1H), 1.91 (m, 2H), 3.41 (m, 4H), 3.86 (m, 1H), 4.52 (s, 2H), 7.33 (m, 5H); $^{13}$ C NMR (CDCl$_3$) δ 138.05, 128.31, 127.58, 74.37, 73.31, 70.60, 34.19, 33.25, 28.58, 25.88, 18.11, −4.34, −4.77; IR (neat): 3025, 2928, 2958, 2856, 2361, 2341 cm$^{-1}$; [α]$_D^{22}$+9.6 (c 1.2, CH$_3$CO$_2$C$_2$H$_5$).

(f) 5-Benzyloxy 4R-t-butyldimethylsiloxy 1-pentyl cyanide (9). To a stirred solution of mesylate 4 (2.00 g, 5 mmol) in DMSO (10 mL) was added NaCN (1.22 g, 25 mmol) and a catalytic amount of 15 crown-5 (1 mL) and then the reaction mixture was heated at 40° C. for 20 hr. The reaction was quenched with water and the solution was extracted with ether. The combined organic layers were washed with brine and dried over MgSO$_4$, then the solvent was removed under reduced pressure to provide the desired pure product (1.54 g, 95%): $^1$H NMR (CDCl$_3$) δ 0.04 (s, 3H), 0.05 (s, 3H), 0.87 (s, 9H), 1.60–1.80 (m, 4H), 2.35 (t, J=6.5 Hz, 2 H), 3.33 (dd, J=9.5, 6.5 Hz, 1H), 3.41 (dd, J=9.5, 5.0 Hz, 1H), 3.84 (m, 1H), 4.51 (s, 2H), 7.31 (m, 5H); $^{13}$C NMR (CDCl$_3$) δ 138.23, 128.33, 127.61, 119.70, 74.05, 73.34, 70.41, 33.56, 25.83, 21.27, 18.11, 17.40, −4.36, −4.81; GC/MS m/z 333 (M$^+$); IR (neat): 3090, 3064, 3031, 2929, 2856 cm$^{-1}$; [α]$_D^{22}$+13.3 (c 0.8, CH$_3$CO$_2$C$_2$H$_5$).

(g) 5-Benzyloxy 4R-t-butyldimethylsiloxy 1-hexanal (2). To a stirred solution of cyanide 9 (1.21 g, 3.74 mmol) in dry CH$_2$Cl$_2$ (30 mL) was added diisobutylaluminum hydride (DIBAL-H, 5.7 mL in 1.0 M Hexanes) at −78° C. and the reaction stirred for 2 hr under N$_2$at rt. Aqueous tartaric acid (10%, 30 mL) was added and mixture was stirred for another 2 hr. The reaction mixture was extracted with CH$_2$Cl$_2$ (2×50 mL) and the solvent was removed under reduced pressure to provide a pure product (1.09 g, 93%): $^1$H NMR (CDCl$_3$) δ 0.05 (s, 3H), 0.06 (s, 3H), 0.87 (s, 9H), 1.42–1.80 (m, 4H), 2.42 (dt, J=1.5, 7.0 Hz, 2H), 3.35 (dd, J=9.5, 5.7 Hz, 1H), 3.41 (dd, J=9.5, 5.4 Hz, 1H), 0.86 (m, 2H), 4.51 (s, 2H), 7.32 (m, 5H), 9.74 (t, J=1.5 Hz, 1H); $^{13}$C NMR (CDCl$_3$) δ 202.39, 138.19, 128.23, 127.52, 127.46, 74.33, 73.25, 70.93, 43.88, 33.99, 25.84, 18.11, 17.79, −4.37, −4.81; IR (neat): 3071, 3030, 2953, 2929, 2856, 1728 cm$^{-1}$; [α]$_D^{22}$+11.8 (c 1.5, CH$_3$CO$_2$C$_2$H$_5$).

(h) 1,11-dibenzyloxy 2R,10S-di-t-(butyldimethylsiloxy) 6-undecanol (10). To a suspension of magnesium powder (0.16 g, 6.7 mmol) in dry ether (2 mL) was added a small piece of iodine under dry N$_2$. After the color of the mixture had turned to gray, the bromide 3 (0.52 g, 1.34 mmol) was added, and the reaction mixture was refluxed for 0.5 h. The mixture was cooled to 0° C. and the aldehyde (0.24 g, 0.67 mmol) was introduced. The reaction was stirred for another 0.5 h at 0° C. and quenched with addition of saturated NH$_4$Cl. The product was extracted with ether. The combined organic layers were washed with brine and dried over anhydrous MgSO$_4$. The solvent was removed under reduced pressure. Flash chromatography of the crude product provided the pure product (Hex/Et$_2$O=6/1 to Hex/EtOAc=6/1; 0.19 g, 45%): $^1$H NMR (CDCl$_3$) δ 0.04 (s, 6H), 0.05 (s, 6H), 0.88 (s, 18H), 1.24–1.63 (m, 13H), 3.36 (m, 4H), 3.57 (m, 1H), 3.80 (m, 2H), 4.52 (s, 4H), 7.26 (m, 10H); $^{13}$C NMR (CDCl$_3$) δ 138.36, 128.25, 127.56, 127.45, 74.62, 73.25, 71.66, 71.37, 37.58, 37.50, 34.66, 25.92, 21.32, 21.24, 18.20, −4.31, −4.69; IR (neat): 3444, 3030, 2932, 2855 cm$^{-1}$; $[\alpha]_D^{22}$+7.0 (c 0.3, CH$_3$CO$_2$C$_2$H$_5$).

(i) 1,11-dibenzyloxy 2R,10S-di-(t-butyldimethylsiloxy) 6-undecanone (1). A solution of oxalyl chloride (0.78 mL, 8.93 mmol) in dry CH$_2$Cl$_2$ (20 mL) was cooled to −78° C. This was followed by the addition of a solution of DMSO (1.27 mL, 17.86 mmol) in dry CH$_2$Cl$_2$ (2 mL). The resulting solution was stirred for 5 min, then a solution of alcohol 10 (5.23 g, 8.12 mmol) in dry CH$_2$Cl$_2$ (2 mL) was added within 2 min, and then stirred for an additional 20 min. Et$_3$N (5.66 mL, 40.60 mmol) was then added and reaction mixture was gradually warmed up to room temperature over 0.5 h at which point it was quenched with water. The two layers were separated and the aqueous layer was extracted with EtOAc. The combined organic layers were dried over MgSO$_4$, and the solvent was removed under reduced pressure. The pure product was obtained by column chromatography (Hex/ EtOAc=10/1, 4.31 g, 83%): $^1$H NMR (CDCl$_3$) δ 0.04 (s, 6H), 0.05 (s, 6H), 0.87 (s, 18H), 1.40–1.70 (m, 8 H), 2.38 (t, J=7.0 Hz, 4H), 3.37 (m, 4H), 3.79 (m, 2H), 4.51 (s, 4H), 7.32 (m, 10H); $^{13}$C NMR (CDCl$_3$) δ 210.69 138.31, 128.23, 127.53, 127.43, 74.48, 73.21, 71.14, 42.71, 34.08, 25.83, 19.50, 18.09, −4.20, −4.82; IR (neat): 3064, 3030, 2955, 2929, 2856, 1714 cm$^{-1}$; $[\alpha]_D^{22}$+11.2 (c 0.4, CHCl$_3$).

(j) Benzyl-protected SPIKET-P1 (SPIKET-P1-P)$^{22}$. To a solution ketone 1 (0.17 g, 0.27 mmol) in CH$_3$CN (4 mL) was added HF (0.42 mL 48% acid) at rt, and the reaction mixture stirred for 1h. EtOAc was added to dilute the reaction, then washed with water, NaHCO$_3$ and brine. The organic layer was dried over anhydrous MgSO$_4$ and solvent was removed under reduced pressure (0.11 g, 100%). $^1$H NMR (CDCl$_3$) δ 1.23–1.67 (m, 10H), 1.91 (m, 2H), 3.47 (m, 4H), 3.90 (m, 2H), 4.59 (s, 4H), 7.32 (m, 10H); $^{13}$C NMR (CDCl$_3$) δ 138.63, 128.23, 127.43, 127.33, 96.19, 73.62, 73.15, 68.57, 35.19, 27.53, 18.53; GC/MS m/z 396 (M$^+$); IR (neat): 3030, 2937, 2855 cm$^{-1}$; $[\alpha]_D^{22}$16.0 (c 0.7, CHCl$_3$).

(k) [2R,8R)-S-(hydroxymethyl)-1,7-dioxaspiro[5,5]undec-2-yl]methan-1ol (SPIKET-P1). To a preformed solution of lithium 4,4'-di-tert-butylbiphenylide (LDBB) $^{23}$ was added dropwise benzylated spiropyran SPIKET-P1-P (0.20 g, 0.51 mmol) in dry THF (1 mL) at 0° C. The mixture immediately changed color from dark blue-greenish to orange. Then after about 0.5 h, the reaction changed back to dark blue-greenish. The reaction was continued for 1h at 0° C. Water was added to quench the reaction and the solution extracted with EtOAc. The combined organic layers dried over anhydrous MgSO$_4$ and the solvent removed under the reduced pressure. The residue was purified by column chromatography (Hex/ EtOAc=2/1, then 100% EtOAc) to give the pure product as a yellowish solid (0.06 g, 50%). $^1$H NMR (CDCl$_3$) δ 1.26–1.53 (m, 6H), 1.63 (m, 4H), 1.88 (m, 2H), 2.14 (bs, 2H), 3.52 (m, 2H), 3.62 (m, 2H), 3.75 (m, 2H); $^{13}$C NMR (CDCl$_3$) δ 95.99, 69.70, 66.16, 35.21, 26.35, 18.24; GC/MS m/z 216 (M$^+$); IR (neat): 3373, 2939, 2871 cm$^{-1}$; $[\alpha]_D^{22}$−59.4 (c 0.7, CHCl$_3$).

X-ray Crystal Structure

The compound, SPIKET-P1, made via the above synthetic pathway was then analyzed with x-ray crystallography. The crystal structure was utilized along with the above characterization data to confirm the structure of SPIKET-P1.

Figure 4:
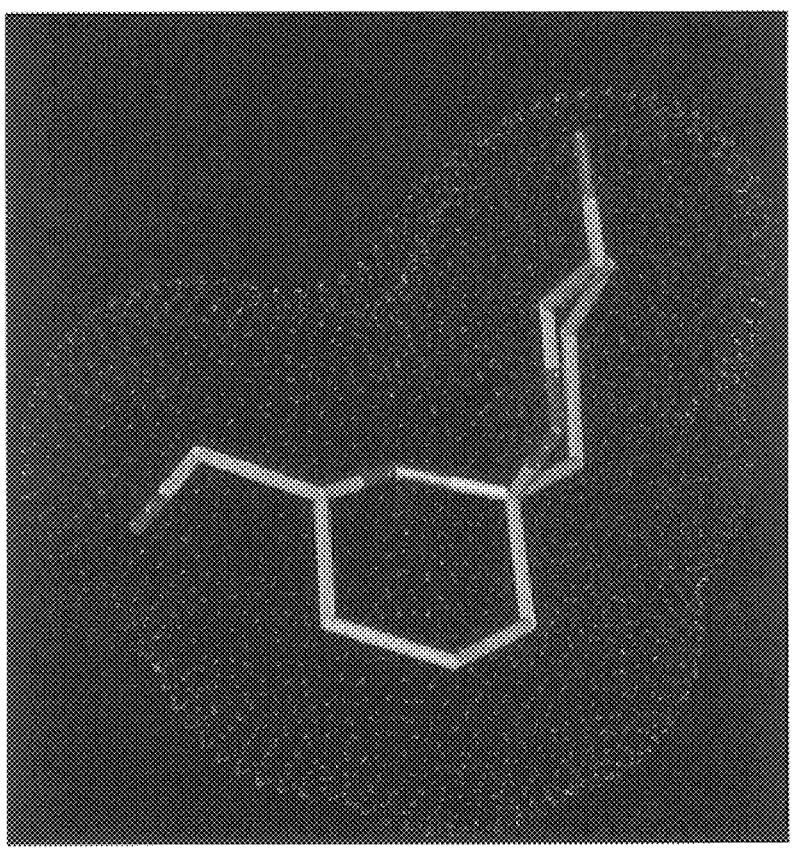
FIG. 4 is a schematic representation of the X-ray structure of SPIKET-P1.
Figure 4:
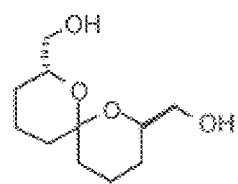

The structure of SPIKET-P1 was confirmed by small molecule X-ray crystallography, as shown in FIG. 4.

| Crystal Data and Structure Refinement for SPIKET-P1 | |
|---|---|
| Crystal Size | 0.05 mm × 0.3 mm × 1 mm |
| Temperature | 298° K. |
| Space Group | P21 |
| | a = 11.4510 Å   a = 90° |
| Unit Cell Dim. | b = 8.9628 Å    b = 93.396° |
| | c = 22.942 Å    g = 90° |
| Volume, Z | 2350.5 Å3, 8 |
| q range | 1.780 to 28.32° |
| Data/Restraints/Parameters | 9044/1/542 |
| GOF on F2 | 1.025 |
| Final R indices [I > 2s(I)] | R1 = 0.1385, wR2 = 0.1754 |

Example 3

Synthesis of Spiroketal, NP25

Another spiroketal was synthesized, NP-25, according to Scheme 3, shown below. The known compound 20, a synthetic intermediate for the synthesis of A&B spiroketal unit of Sp,$^{12}$ was treated with hydrofluoric acid to afford NP-25. As shown in Scheme 3, following monoalkylation of 1,3-propandiol 11 by benzyl chloride, Swern oxidation of the alcohol 12 gave the aldehyde 13. Addition of the allylborane to 13 gave, after oxidative workup, the homoallylic alcohol 14. Silyl protection of 14 as the TES ether gave 15. Reaction of 15 with osmium tetroxide and sodium periodate, gave the (S)-aldehyde 16. Following enolisation of acetone with (−)-Ipc$_2$BCl, addition of the boron enolate to 16 produced methyl ketone alcohol 17. After silyl protection of 17 as TBS ether to obtain 18, using the boron enolate prepared from 18 and (−)-Ipc$_2$BCl to couple with 16 gave 19. Treatment of 19 with PPTS in methanol/ dichloromethane led to clean removal of both TES protecting groups and in situ acetalisation to produce a single spiroketal 20. Treatment of 20 with hydrofluoric acid in tetrahydrofuran led to removal of TBS protecting group to give dihydroxy spiroketal NP-25.

Scheme 3:

Synthesis of Spiroketal, NP-25

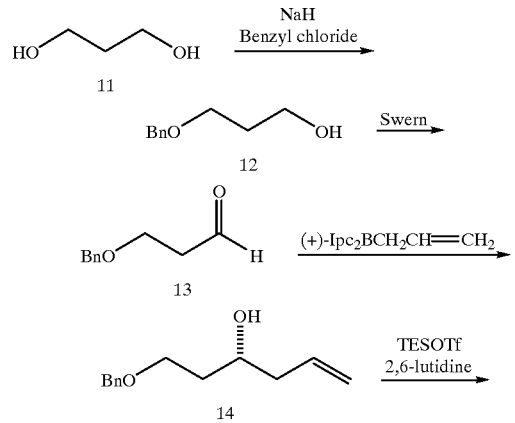

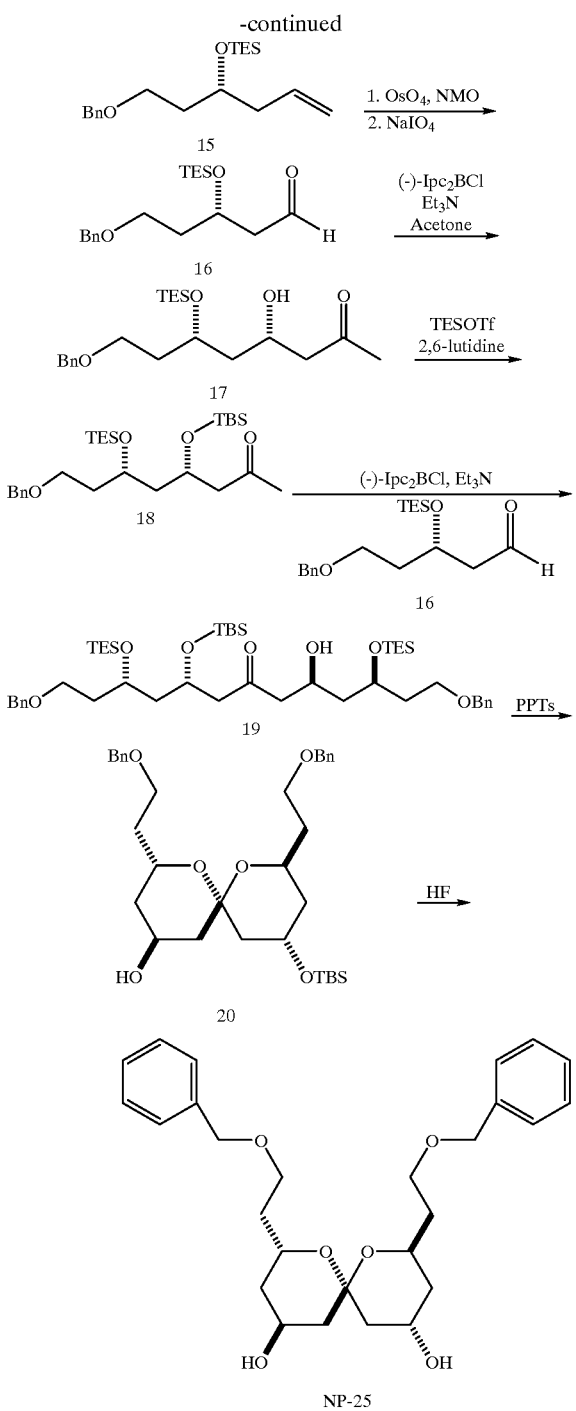

The detailed method for the synthesis of NP-25 is given below. The step is referred to by the intermediate product that it produces. Characterization data for each intermediate product is also given. The structures can be seen in Scheme 3 above.

3-Benzyloxy-1-propanol (12). To a solution of 50.0 g (0.657 mol) of 1,3-propandiol 11 in 500 mL of cosolvent (DMF : THF=3:1) in an ice bath was carefully added 26.3 g (0.657 mol) of 60% sodium hydride and stirred for 1 hour, followed by slow addition of 80.5 g (0.636 mol) of benzyl chloride at 0° C. and stirring at room temperature overnight. After adding 50 mL of water to quench the reaction, the mixture was extracted with ether (2×600 mL). The organic layer was washed with water (50 mL) and Brine (50 mL), dried over anhydrous sodium sulfate and concentrated. Distillation at 118–120° C./5 mmHg gave 54.8 g of a liquid in 50.2% yield. $^1$H NMR (CDCl$_3$): δ 7.35–7.28 (m, 5H, ArH), 4.51 (s, 2H, ArCH$_2$O), 3.76 (m, 2H, CH$_2$O), 3.65 (t, J=6.0 Hz, 2H, CH$_2$O), 2.58 (m, 1H, OH), 1.85 (p, J=6.0 Hz, 2H, CH2). $^{13}$C NMR (CDCl$_3$): δ 137.93, 128.34, 127.60, 127.54, 73.15, 69.15, 61.58, 32.04.

3-Benzyloxy-propionaldehyde (13). To a solution of 15.6 mL of oxalyl chloride in 420 mL of dichloromethane at −78° C. was added 24.0 mL of dimethyl sufoxide and stirred for 10 min, followed by addition of 19.95 g (0.12 mol) of 3-benzyloxy-1-propanol and stirred for 45 min. After adding 58.5 mL of triethylamine, the mixture was stirred in an ice bath for 20 min. 42 mL of water was added and the mixture was extracted with 660 mL of benzene/diethyl ether (1/1). The organic layer was washed with 5% hydrochloric acid (42 mL), water (42 mL) and brine (42 mL), dried over anhydrous sodium sulfate and concentrated. Distillation at 68–70° C./3 mmHg gave 17.0 g of a liquid in 86.3% yield. $^1$H NMR (CDCl$_3$): δ 9.79 (t, J=1.8 Hz, 1H, CHO), 7.35–7.31 (m, 5H, ArH), 4.53 (s, 2H, ArCH$_2$O), 3.81 (t, J=6.0 Hz, 2H, CH$_2$O), 2.69 (td, J=6.0, 1.8 Hz, 2H, CH$_2$C=O). $^{13}$C NMR (CDCl$_3$): δ 201.08, 137.72, 128.35, 127.69, 127.62, 73.18, 63.75, 43.81. EIMS m/z 164 (M$^+$), 107, 91, 79.

4-Hydroxy-6-benzyloxy-1-hexene (14). To a solution of 37.98 g (0.118 mmol) (+)-B-methoxydiisopinocampheylborane in 120 mL diethyl ether at −78° C. was dropwise added 120 mL (0.120 mol) of allylmagnesium bromide (1.0 M in diethyl ether), and stirred for 15 min at −78° C. and 1 h at room temperature. After addition of 17.0 g (10.4 mmol) of 3-benzyloxy-propionaldehyde at −78° C., the mixture was stirred for 1 hour at −78° C. and 1 hour at room temperature. To the mixture were added 90 mL of 3N sodium hydroxide and 36 mL of 30% hydrogen peroxide and heated at reflux for 1 h. The aqueous layer was separated and the organic layer was washed with water (75 mL) and brine (75 mL), dried over anhydrous sodium sulfate and concentrated. Following distillation of the residue to remove isopinocampheol, flash column chromatography (hexanes: ethyl acetate=5:1) gave 15.5 g of a liquid in 70.2% yield. $^1$H NMR (CDCl$_3$): δ 7.36–7.28 (m, 5H, ArH), 5.83 (m, 1H, CH=C), 5.12 (m, 2H, C=CH$_2$), 4.52 (s, 2H, ArCH$_2$O), 3.88 (m, 1H, CH-O), 3.73 (m, 2H, CH$_2$O), 2.91 (d, J=2.4 Hz, 1H, OH), 2.25 (m, 2H, CH$_2$), 1.76 (m, 2H, CH$_2$). $^{13}$C NMR (CDCl$_3$): 137.84, 134.80, 128.40, 127.69, 127.62, 117.55, 73.29, 70.38, 68.95, 41.91, 35.82. HRMS (CI, NH$_3$) found: 207.1388, calcd for C$_{13}$H$_{19}$O$_2$ (M+H)$^+$: 207.1385.

4-Triethylsilyloxy-6-benzyloxy-1-hexene (15). To a solution of 10.52 g (51.0 mmol) of 4-hydroxy-6-benzyloxy-1-hexene in 300 mL of dichloromethane at −78° C. was added 23.75 mL (204.0 mmol) of 2,6-lutidine and stirred for 10 min, followed by addition of 23.24 mL (102.0 mmol) of triethylsilyl trifluoromethanesulfonate and stirring for 2 hours. The mixture was partitioned between 750 mL of diethyl ether and 500 mL of water. The organic layer was washed with 1N hydrochloric acid (380 mL), water (380 mL) and brine (380 mL), dried over anhydrous sodium sulfate and concentrated. The residue was purified by flash column chromatography (hexanes : ethyl acetate=200:3) to give 13.71 g of a liquid in 83.9% yield. [α]$^{22}{}_D$−11.69° (c 3.15, CHCl$_3$). IR (KBr): 3074, 3030, 2955, 2977 cm$^{−1}$. $^1$H NMR (CDCl$_3$): δ 7.34–7.25 (m, 5H, ArH), 5.77 (m, 1H, CH=C), 5.05 (m, 2H, C=CH$_2$), 4.52 (d, J=11.7 Hz, 1H, ArCH$_2$O), 4.46 (d, J=11.7 Hz, 1H, ArCH$_2$O), 3.91 (m, 1H, CH—O), 3.54 (m, 2H, CH$_2$O), 2.21 (m, 2H, CH$_2$), 1.75 (m, 2H, CH$_2$), 0.96 (t, J=8.1 Hz, 9H, TES CH$_3$), 0.60 (q, J=8.1 Hz, 6H, TES CH$_2$). $^{13}$C NMR (CDCl$_3$): 138.46, 134.83, 128.27, 127.63, 127.43, 116.99, 72.95, 68.94, 66.99, 42.41, 36.80, 6.95, 5.02. HRMS (CI, NH$_3$) found: 321.2251, calcd for C$_{19}$H$_{33}$O$_2$Si (M+H)$^+$: 321.2250.

3-Triethylsilyloxy-5benzyloxy-valeraldehyde (16). To a solution of 10.0 g (31.2 mmol) of 4-Triethylsilyloxy-6-benzyloxy-1-hexene in 310 mL of tetrahydrofuran at 0° C. were added 4.38 g (37.4 mmol) of 4-methylmorpholine N-oxide, 6.24 mL (1.248 mmol) of osmium tetroxide (0.2M in benzene) and 45 mL of water and stirred overnight at room temperature. To the mixture at 0° C. were added 185 mL of water and 20.02 g (93.6 mmol) of sodium periodate and stirred at room temperature for 1 hour, followed by partitioned between ethyl acetate and water. The organic layer was washed with water and brine, dried over anhydrous sodium sulfate and concentrated for the next reaction. $^1$H NMR (CDCl$_3$): δ 9.79 (t, J=2.4 Hz, 1H, CH=O), 7.35–7.31 (m, 5H, ArH), 4.51 (d, J=12.0 Hz, 1H, ArCH$_2$O), 4.46 (d, J=12.0 Hz, 1H, ArCH$_2$O), 4.40 (p, J=6.0 Hz, 1H, CH—O), 3.55 (m, 2H, CH$_2$—O), 2.56 (m, 2H, CH$_2$C=O), 1.85 (m, 2H, CH$_2$), 0.94 (t, J=8.1 Hz, 9H, TES CH$_3$), 0.59 (q,J=8.1 Hz, 6H, TES CH$_2$). $^{13}$CNMR (CDCl$_3$): δ 201.94, 138.14, 128.31, 127.60, 127.55, 72.99, 66.31, 65.49, 51.14, 37.71, 6.84, 4.88.

4-Hydroxy-6-triethylsilyloxy-8-benzyloxy-hexan-2-one (17). To a solution of 26.02 g (81.1 mmol) of (-)-B-chlorodiisopinocampheylborane in 150 mL of dry diethyl ether at 0° C. were added 12.63 g (12.5 mmol) of triethylamine and 3.63 g (62.5 mmol) of acetone, and stirred for 30 min, followed by addition of 31.2 mmol of 3-triethylsilyloxy-5-benzyloxy-valeraldehyde at −78° C. and stirring for 5 hours. The mixture was partitioned between diethyl ether (430 mL) and pH 7 buffer (310 mL). The organic layer was concentrated and the residue was dissolved in 310 mL of methanol. To the solution at 0° C. were added pH 7 buffer (62 mL) and 30% hydrogen peroxide (94 mL) and stirred at room temperature for 1–2 h. The mixture was diluted with 500 mL of water and extracted with dichloromethane (3×500 mL). The organic layer was washed with sodium bicarbonate solution and brine, dried over anhydrous sodium sulfate and concentrated. The residue was purified by flash column chromatography (Hexanes:ethyl acetate=4:1) to give 7.2 g of a liquid in 60.6% yield for two steps. $[\alpha]^{22}{}_D$+8.63° (c 1.10, CHCl$_3$). IR (KBr): 3417 (br), 3037, 2955, 2886, 1713 cm$^{-1}$. $^1$H NMR (CDCl$_3$): δ 7.35–7.31 (m,5H,ArH), 4.51 (d, J=11.7 Hz, 1H, ArCH$_2$—O), 4.46 (d, J=11.7 Hz, 1H, ArCH$_2$O), 4.20 (m, 1H, CH—O), 4.19 (m, 1H, CH—O), 3.53 (t, J=6.3 Hz, 2H, CH$_2$O), 2.55 (m, 2H, CH$_2$—C=O), 2.16 (s, 3H, CH$_3$—C=O), 1.83 (q, J=6.3 Hz, 2H, CH$_2$), 1.60 (m, 2H, CH$_2$), 0.96 (t, J=8.1 Hz, 9H, TES CH$_3$), 0.62 (q, J=8.1 Hz, 6H, TBS CH$_2$). $^{13}$C NMR (CDCl$_3$): δ 208.93, 138.28, 128.30, 127.63, 127.52, 72.98, 69.08, 66.56, 66.20, 50.62, 43.02, 37.22, 30.77, 6.80, 4.94. HRMS (Cl NH$_3$) found: 381.2473, calcd for C$_{21}$H$_{37}$O$_4$Si (M+H)$^+$: 381.2461.

4-tert-Butyldimethylsilyloxy-6-triethylsilyloxy-8-benzyloxy-hexan-2-one (18). To a solution of 7.0 g (18.4 mmol) of 4-hydroxy-6-triethylsilyloxy-8-benzyloxy-hexan-2-one 17 in dry tetrahydrofuran at −78° C. was added 7.89 g (73.6 mmol) of 2,6-lutidine and stirred for 10 min, followed by addition of 9.73 g (36.8 mmol) of tert-butyldimethylsilyl trifluoromethanesulfonate and stirring for 2 hours. The mixture was partitioned between diethyl ether (300 mL) and water (200 mL). The organic layer was washed with 130 mL of 5% hydrochloric acid, 130 mL of water and 130 mL of brine, dried over anhydrous sodium sulfate and concentrated. The residue was purified by flash column chromatography (hexanes: ethyl acetate=20:1) to give 5.69 g of a liquid in 62.5% yield. $[\alpha]^{22}{}_D$−0.740° (c 1.99, CHCl$_3$). IR (KBr): 2957, 2877, 1720 cm$^{-1}$. $^1$H NMR (CDCl$_3$): δ 7.33–7.28 (m, 5H, ArH), 4.48 (d, J=11.7 Hz, 1H, ArCH$_2$O), 4.44 (d, J=11.7 Hz, 1H, ArCH$_2$O), 4.23 (p, J=6.0 Hz, 1H, CH—O), 3.92 (m, 1H, CH—O), 3.52 (m, 2H, CH$_2$—O), 2.55 (d, J=6.0 Hz, 2H, CH$_2$C=O), 2.12 (s, 3H, CH$_3$C=O), 1.84–1.54 (m, 4H, CH$_2$), 0.93 (t, 9H, TES CH$_3$), 0.83 (s, 9H, TBS CH$_3$), 0.57 (q, J=8.1 Hz, 6H, TES CH$_2$), 0.03 (s, 3H, TBS CH$_3$), 0.00 (s, 3H, TBS CH$_3$). $^{13}$C NMR (CDCl$_3$): δ 207.56, 138.48, 128.26, 127.64, 127.43, 72.97, 66.76, 66.63, 66.41, 51.29, 45.42, 37.13, 31.61, 25.78, 17.88, 6.93, 501, −4.57, −4.69. HRMS(CI, NH$_3$)found: 495.3342, calcd for C$_{27}$H$_{51}$, O$_4$Si$_2$ (M+H)$^+$:495.3326.

1,13-dibenzyloxy-3,11-di(triethylsilyloxy)-5-tert-butyldimethylsilyloxy-9-hydroxy-tridecan-7-one (19). The similar method in synthesis of compound (17) was used. $^1$H NMR (CDCl$_3$): δ 7.35–7.26 (m, 10H, ArH), 4.48 (m, 4H, ArCH$_2$O), 4.30–4.09 (m, 4H, CH—O), 3.93 (m, 1H OH), 3.55–3.50 (m, 4H, CH$_2$—O), 2.58–2.52 (m, 4H, CH$_2$C=O), 1.89–1.56 (m, 8H, CH$_2$), 0.95 (m, 18H, TES CH$_3$), 0.84 (s, 9H, TBS CH$_3$), 0.61 (m, 12H, TES CH$_2$), 0.05 (s, 3H, TBS CH$_3$), 0.01 (s, 3H, TBS CH$_3$). $^{13}$C NMR (CDCl$_3$): δ 209.57, 138.42, 138.30, 128.25, 127.58, 127.45, 127.38, 72.93, 68.68, 66.68, 66.62, 66.13, 65.77, 51.48, 51.12, 45.40, 43.26, 37.08, 25.75, 17.81, 6.88, 6.80, 4.96, 4.92, −4.62, −4.71.

1,13-dibenzyloxy-5-tert-butyldimethylsilyloxy-9-hydroxy-spiroketal (20). To a solution of 150 mg of 3 in 2 mL of dichloromethane and 2 mL of methanol was added 5 mg of pyridinium p-toluenesulfonate and stirred for 3 h. The mixture was partitioned between ethyl acetate and water. The organic layer was washed with water, sodium bicarbonate solution and brine, dried over anhydrous sodium sulfate and concentrated. The residue was purified by flash chromatography to give 80 mg of a liquid in 76.2% yield. $[\alpha]^{22}{}_D$−49.69° (c 1.68, CHCl$_3$). IR (KBr): 3521, 3029, 2926 cm$^{-1}$. $^1$H NMR (CDCl$_3$): δ 7.27–7.20 (m, 10H, ArH), 4.36 (m, 4H, ArCH$_2$O), 4.13 (m, 1H, OH), 4.04 (m, 2H, CH$_2$—O), 3.98 (br s, 2H, CH$_2$), 3.60 (m, 2H, CH—O), 3.41 (m, 2H, CH—O), 1.77–1.61 (m, 6H, CH$_2$), 1.57–1.36 (m, 6H, CH$_2$), 0.86 (s, 9H, TBS CH$_3$), 0.00 (s, 6H, TBS CH$_3$). $^{13}$C NMR (CDCl$_3$): δ 138.68, 138.20, 128.24, 128.21, 127.91, 127.52, 127.45, 127.36, 98.20, 73.03, 72.83, 67.77, 67.16, 65.16, 64.34, 63.15, 60.95, 41.23, 40.69, 38.65, 37.99, 35.87, 35.77, 25.88, 18.20, −4.73, −4.97. HRMS (CI NH3) m/z 571.3553 (M+H)$^+$, calcd for C$_{33}$H$_{31}$O$_6$Si 571.3455; 588.3717 (M+NH$_4$)$^+$, calcd for C$_{33}$H$_{34}$NO$_6$Si 588.3720; 553.3347 (M−OH)$^+$, calcd for C$_{33}$H$_{29}$O$_5$Si 553.3349.

1,13-dibenzyloxy-5,9-dihydroxy-spiroketal (NP25). To a solution of 40 mg of 20 in 2.5 mL acetonitrile was added 0.26 mL of 48% hydrofluoric acid and stirred at room temperature for 1.5 hours. The mixture applied to flash chromatography column and purified in the present of triethylamine to give 30 mg of a liquid in 93.8% yield. $^1$H NMR (CDCl$_3$): 7.32–7.26 (m, 10H, ArH), 4.46 (d, J=12.0 Hz, 2H, ArCH$_2$O), 4.39 (d, J=12.0 Hz, 2H, ArCH$_2$O), 4.26 (d, J=9.0 Hz, 2H, OH), 4.14 (m, 2H, CH—O), 4.04 (m, 2H, CH—O), 3.43 (t, 4H, CH$_2$OBn), 1.88–1.73 (m, 6H, CH$_2$), 1.67–1.48 (m, 6H, $^{13}$C NMR (CDCl$_3$): 138.02, 128.20, 128.06, 127.53, 99.76, 73.17, 67.48, 64.43, 63.32, 39.78, 38.16, 35.52.

Example 4

Effects of SPIKETs on Tubulin Polymerization

The ability of SPIKET-P1, its benzyl-protected precursor SPIKET-P1P, and the natural analog NP-25 to cause tubulin depolymerization or to prevent tubulin polymerization was next analyzed. Bovine brain tubulin (Sigma, St. Louis, Mo.) was used in standard turbidity assays to test the effects of SPIKET-P1, SPIKET-P1-P and NP-25 on GTP-induced tubulin polymerization.

Compounds (in 1% DMSO) were added to tubulin (1 mg/mL, 0.1M MES, 1 mM EGTA, 0.5 mM MgCl2, 0.1 mM EDTA, 2.5M glycerol, 1 mg/ml leupeptin, 1 mg/ml aprotinin, pH 6.5) followed by stimulation of polymerization with 1 mM GTP at 2 minutes. Optical density was measured using a Becton Dickinson WV spectrophotometer at 350 nm using a thermostated cuvette holder to keep the reaction at 37° C. Readings obtained from the spectrophotometer were standardized by subtracting the background absorbance of the compound in water from the sample reading following drug addition.

Figure 5:
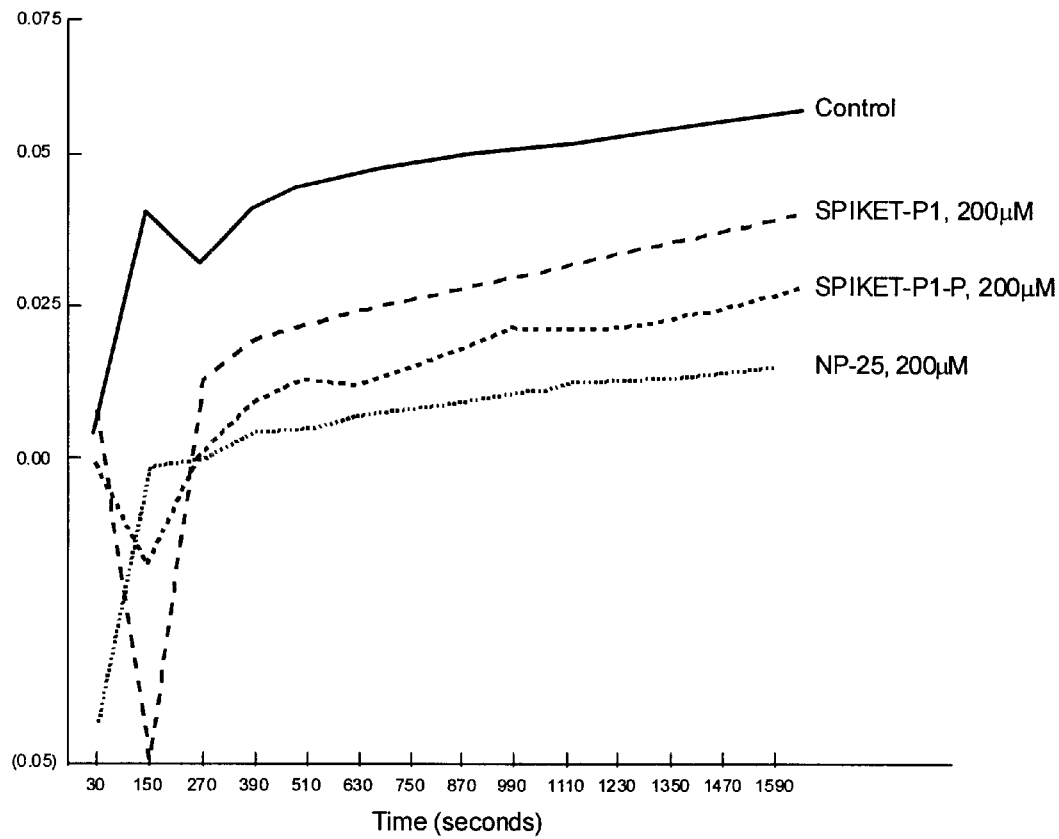
FIG. 5 is a graph showing the anti-tubulin activity of the compounds of the invention as analyzed in turbidity assays.

The results are shown in FIG. 5, and indicate all three tested SPIKET compounds caused partial depolymerization of tubulin and inhibited GTP-induced tubulin polymerization.

Example 5

Induction of Cancer Cell Apoptosis by SPIKETs

The effects of spiroketal pyrans on the survival of human breast cancer cells were examined in vitro. Cells were incubated at 37° C. for the indicated time periods with the title compounds. At the end of the incubation, cells were washed twice with PBS and fixed in 2% paraformaldehyde. and examined by microscopy.

Figure 6:
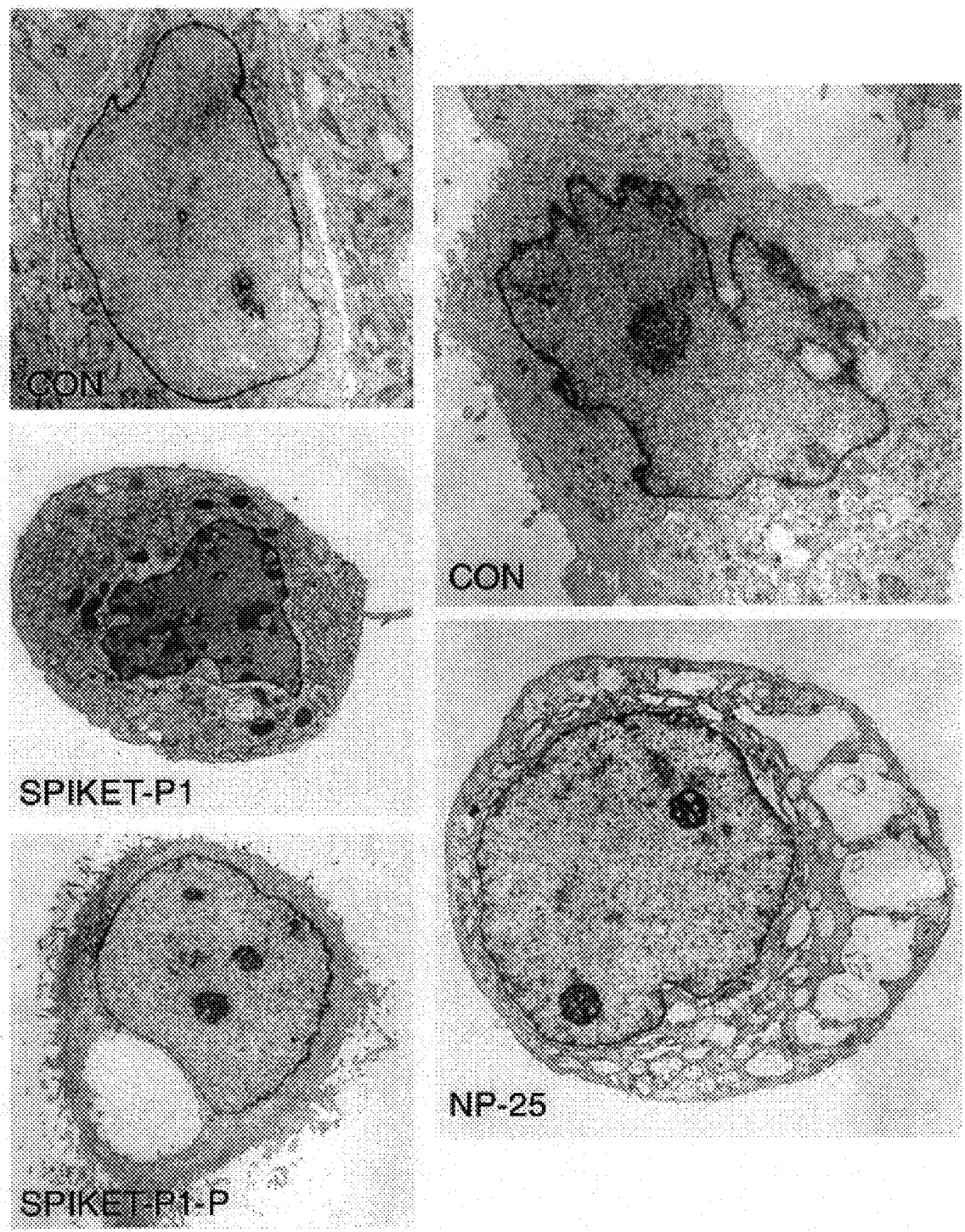
FIGS. 6A–6E are electron micrographs showing induced apoptosis in control (FIGS. 6A and 6B), SPIKET-P1 (FIG. 6C), SPIKET-P1P (FIG. 6D), and NP-25 (FIG. 6E)treated human breast cancer cells.

FIG. 6 shows human BT-20 breast cancer cells that were treated with SPIKET-P1, SPIKET-P1-P, or NP-25 by transmission electron microscopy[13]. The data provide direct evidence that these compounds induce apoptosis in human breast cancer cells.

The effects of SPIKET-P1 on human breast cancer cells was also examined using confocal laser scanning microscopy[14]. After fixing, the cells were permeabilized and non-specific binding sites were blocked with 2.5% BSA in PBS containing 0.1% Triton X-100 for 30 minutes. Tubulin expression was examined by immunofluorescence using a monoclonal antibody against a-tubulin (Sigma Chemical Co, St. Louis, Mo.) at a dilution of 1:1000 and an anti-mouse IgG conjugated to FITC. Cells were washed in PBS and counterstained with toto-3 (Molecular Probes Inc., Eugene, Oreg.) for 10 minutes at a dilution of 1:1000. Cells were washed again with PBS and the coverslips were mounted with Vectashield (Vector Labs, Burlingame, Calif.) and viewed with a confocal microscope (Bio-Rad MRC 1024) mounted in a Nikon Labhophot upright microscope.

Figure 7:
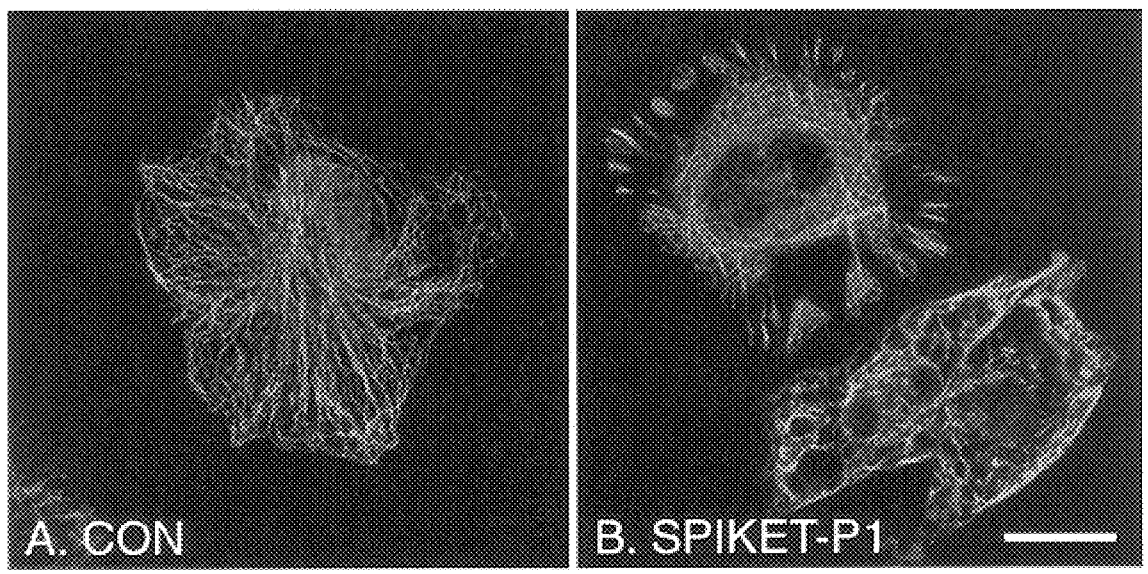
FIGS. 7A and 7B are confocal microscopic images showing the effects of SPIKET-P1 on microtubules in human breast cancer cells. Control (FIG. 7A) and treated cells (FIG. 77B) show microtubules as green fluoresence, DNA as blue. The Bar indicates a size of 20 microns.

Digital images were saved on a Jaz disk and processed with Adobe Photoshop software (Adobe Systems, Mountain View, Calif.). As shown in FIGS. 7A-7B, SPIKET-P1 treated cells showed destruction of the microtubule organization, membrane blebbing, and nuclear fragmentation consistent with apoptosis.

Vehicle-treated control cells are adherent with a well organized microtubule cytoskeleton, seen in the control (FIG. 7A) in green. In contrast, cells treated with 500 mM SPA-1 (FIG. 7B) for 24 hours showed fewer, less organized microtubules. Additionally, membrane blebbing and nuclear fragmentation was observed. Large vacuoles were present within treated cells. SPIKET-P-1 also affected the mitotic index, 2.25% of control cells were in mitosis whereas 0.0% of treated cells were in mitosis (23/1024 vs 0/1000, respectively).

Example 6

SPIKET Combinatorial Libraries

The modeling studies discussed above revealed that the SP binding pocket of tubulin has sterically available space around the docked SPIKET-P1 molecule (see FIG. 3). The introduction of hydrophobic substituents into this SP pharmacophore could therefore result in enhanced biologic activity by increasing the contact surface with the SP binding pocket of tubulin.

To test this hypothesis, we synthesized a series of SPIKET-P-1 based bi-ester libraries by solution-phase combinatorial chemistry, including 2 model libraries (Table 1), 2 mono-ester libraries (Table 2 and 4) and 14 bi-ester libraries (Table 3 and Table 5). Our combinatorial synthetic strategy is illustrated in Scheme 4.

Scheme 4:

Syntehsis of SPIKET-P1 based mono and bi-ester libraries.

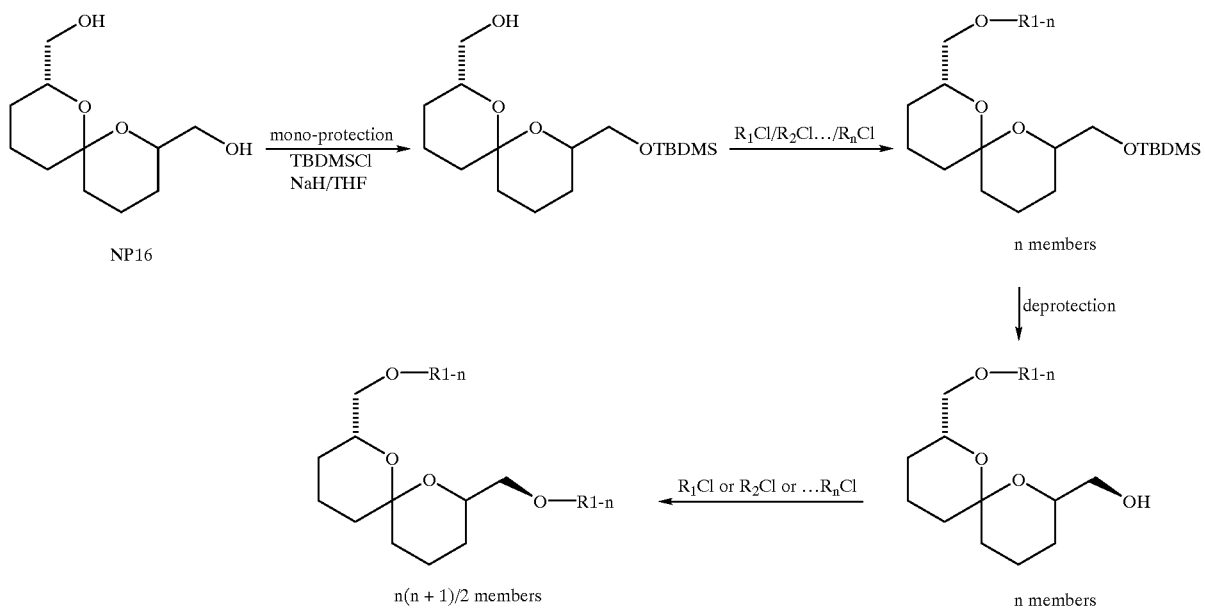

-continued

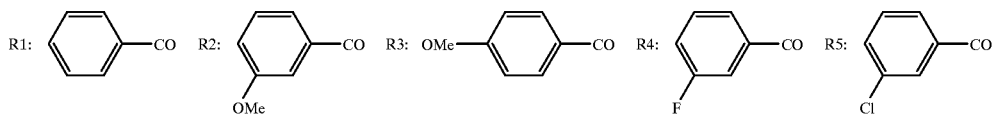

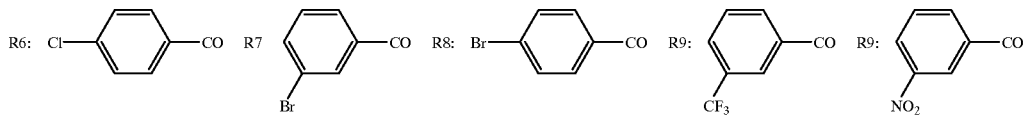

TABLE 1

Members of model libraries HHML3 and HHML4

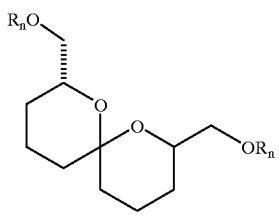

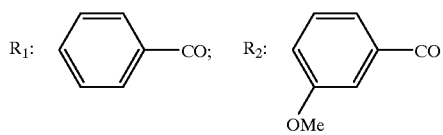

| Name | number of compounds | Structure |
|---|---|---|
| HHML3 | 2 | MW1: 424.25, MW2: 455.26, Avg MW: 439.76<br>GC-MS: 424 (M⁺), 454 (M − 1)⁺ |
| HHML4 | 2 | MW1: 486.27, MW2: 455.26, Avg MW: 470.77<br>GC-MS: 454 (M − 1)⁺, 484 (M − 2)⁺ |

Both model libraries HHML3 and HHML4 contain almost equal molar amounts of the two members. Of these two model libraries, HHML3 exhibited more potent tubulin depolymerizing activity in standard tubulin turbidity assays.

TABLE 2

Theoretical number of members of mono-ester library (HHL2)

[Structure: bicyclic spiroketal with $OR_{1-10}$ group and $CH_2OH$ group]

MW average = 361.96

| $R_n$ | Structure | Formula | MW |
|---|---|---|---|
| $R_1$ | phenyl-CO | $C_{18}H_{24}O_5$ | 320.18 |
| $R_2$ | 3-OMe-phenyl-CO | $C_{19}H_{26}O_6$ | 350.19 |
| $R_3$ | 4-OMe-phenyl-CO | $C_{19}H_{26}O_6$ | 350.19 |
| $R_4$ | 3-F-phenyl-CO | $C_{18}H_{23}O_5F$ | 338.18 |
| $R_5$ | 3-Cl-phenyl-CO | $C_{18}H_{23}O_5Cl$ | 354.68 |
| $R_6$ | 4-Cl-phenyl-CO | $C_{18}H_{23}O_5Cl$ | 354.68 |
| $R_7$ | 3-Br-phenyl-CO | $C_{18}H_{23}O_5Br$ | 399.08 |
| $R_8$ | 4-Br-phenyl-CO | $C_{18}H_{23}O_5Br$ | 399.08 |
| $R_9$ | 3-$CF_3$-phenyl-CO | $C_{19}H_{23}O_5F_3$ | 388.19 |
| $R_{10}$ | 3-$NO_2$-phenyl-CO | $C_{18}H_{23}O_7N$ | 365.18 |

Our GC-MS analysis showed the presence of 9 of the 10 expected member compounds in this library ($R_3$ in the table: p-substituted MeO compound was missing).

TABLE 3

**Theoretical number of members of bi-ester libraries HHL2a–j*:
10 libraries, each has 10 members.**

[Structure: bicyclic spiroketal with two $OR_{1-10}$ groups]

| Lib | MW | R1 | R2 | R3 | R4 | R5 | R6 | R7 | R8 | R9 | R10 |
|---|---|---|---|---|---|---|---|---|---|---|---|
| HHL2a | R1 | 424.25 GC-MS $M^+$ | 454.26 GC-MS $M^+$ | 454.26 GC-MS $M^+$ | 442.25 GC-MS $M^+$ | 458.75 GC-MS $M^+$ | 458.75 GC-MS $M^+$ | 503.15 GC-MS $M^+$ | 503.15 GC-MS $M^+$ | 492.26 GC-MS $M^+$ | 469.25 GC-MS $M^+$ |
| HHL2b | R2 | | 484.27 GC-MS $M^+$ | 484.27 GC-MS $M^+$ | 472.26 GC-MS $M^+$ | 488.76 GC-MS $M^+$ | 488.76 GC-MS $M^+$ | 533.16 GC-MS $(M+1)^+$ | 533.16 GC-MS $(M+1)^+$ | 522.27 GC-MS $M^+$ | 499.26 GC-MS $M^+$ |
| HHL2c | R3 | | | 484.27 GC-MS $M^+$ | 472.26 GC-MS $M^+$ | 488.76 GC-MS $M^+$ | 488.76 GC-MS $M^+$ | 533.16 GC-MS $M^+$ | 533.16 GC-MS $(M-1)^+$ | 522.27 GC-MS $(M-1)^+$ | 499.26 GC-MS $M^+$ |

TABLE 3-continued

Theoretical number of members of bi-ester libraries HHL2a–j*:
10 libraries, each has 10 members.

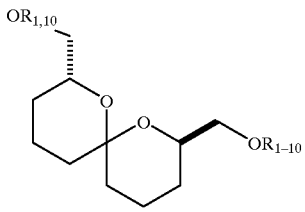

| Lib | MW | R1 | R2 | R3 | R4 | R5 | R6 | R7 | R8 | R9 | R10 |
|---|---|---|---|---|---|---|---|---|---|---|---|
| HHL2d | R4 | | | | 460.25 GC-MS M+ | 476.75 GC-MS M+ | 476.75 GC-MS M+ | 521.15 GC-MS M+ | 521.15 GC-MS (M + 1)+ | 510.26 GC-MS (M + 1)+ | 487.25 GC-MS M+ |
| HHL2e | R5 | | | | | 493.25 GC-MS (M − 1)+ | 493.25 GC-MS (M − 1)+ | 537.65 GC-MS M+ | 537.65 GC-MS M+ | 526.76 GC-MS M+ | 503.75 GC-MS M+ |
| HHL2f | R6 | | | | | | 493.25 GC-MS (M − 1)+ | 537.65 GC-MS (M − 1)+ | 537.65 GC-MS M+ | 526.76 GC-MS M+ | 503.75 GC-MS M+ |
| HHL2g | R7 | | | | | | | 582.05 GC-MS M+ | 582.05 GC-MS M+ | 571.16 GC-MS M+ | 548.15 GC-MS M+ |
| HHL2h | R8 | | | | | | | | 582.05 GC-MS M+ | 571.16 GC-MS M+ | 548.15 GC-MS M+ |
| HHL2i | R9 | | | | | | | | | 560.27 GC-MS M+ | 537.26 GC-MS M+ |
| HHL2j | R10 | | | | | | | | | | 514.25 GC-MS M+ |

*HHL2a: fixed one ester group to R1, vary the other ester group from R1 to R10,
HHL2b: fixed one ester group to R2, vary the other ester group from R1 to R10,
HHL2j: fixed one ester group to R10, vary the other ester group from R1 to R10, The molecular weight in Table 3 was symmetrical along the diagonal axis. GC-MS showed that there were only 9 members ($R_3$ was missing) in each of the 10 sublibraries.

The sublibraries HHL2c and HHL2f exhibited potent tubulin depolymerizing activity in tubulin turbidity assays (FIG. 8), which was superior to that of SPIKET-P1.

TABLE 4

Members of Mono-ester library (HHL4):

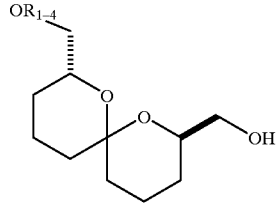

| $R_n$ | Structure | Formula | MW (average is 346.44) |
|---|---|---|---|
| $R_1$ | ⌬—CO | $C_{18}H_{24}O_5$ | 320.18 |

TABLE 4-continued

Members of Mono-ester library (HHL4):

| $R_n$ | Structure | Formula | MW (average is 346.44) |
|---|---|---|---|
| $R_2$ | OMe-⌬-CO (meta) | $C_{19}H_{26}O_6$ | 350.19 |
| $R_3$ | OMe-⌬-CO (para) | $C_{19}H_{26}O_6$ | 350.19 |

TABLE 4-continued

Members of Mono-ester library (HHL4):

| $R_n$ | Structure | Formula | MW (average is 346.44) |
|---|---|---|---|
| $R_4$ | (3-nitrobenzoyl) | $C_{18}H_{23}O_7N$ | 365.18 |

TABLE 5

GC-MS confirmed the presence of 4 member compounds in the library.
Members of bi-ester libraries HHL4a–d*:
4 libraries, each has 4 members R1: benzoyl (–CO–C₆H₅)
R2: 3-methoxybenzoyl
R3: 4-methoxybenzoyl
R4: 3-nitrobenzoyl

| Lib | MW | R1 | R2 | R3 | R4 |
|---|---|---|---|---|---|
| HHL4a | R1 | 424.25 GC-MS M⁺ | 454.26 GC-MS M⁺ | 454.26 GC-MS M⁺ | 442.25 GC-MS M⁺ |
| HHL4b | R2 | | 484.27 GC-MS M⁺ | 484.27 GC-MS M⁺ | 472.26 GC-MS M⁺ |
| HHL4c | R3 | | | 484.27 GC-MS M⁺ | 472.26 GC-MS M⁺ |
| HHL4d | R4 | | | | 460.25 GC-MS M⁺ |

*HHL4a: fixed one ester group to R1, vary the other ester group from R1 to R4,
HHL4b: fixed one ester group to R2, vary the other ester group from R1 to R4,
HHL4c: fixed one ester group to R3, vary the other ester group from R1 to R4,
HHL4d: fixed one ester group to R4, vary the other ester group from R1 to R4,

TABLE 1

1,11-dibenzoate-spiroketal
1,11-di-m-methoxybenzoate-spiroketal
1-benzoate-11-m-methoxybenzoate-spiroketal
11-benzoate-1-m-methoxybenzoate-spiroketal

TABLE 2

1-methanol-11-benzoate-spiroketal
1-methanol-11-m-methoxybenzoate-spiroketal
1-methanol-11-p-methoxylbenzoate-spiroketal
1-methanol-11-m-fluorobenzoate-spiroketal
1-methanol-11-m-chlorobenzoate-spiroketal
1-methanol-11-p-chlorobenzoate-spiroketal
1-methanol-11-m-bromobenzoate-spiroketal
1-methanol-11-p-bromobenzoate-spiroketal
1-methanol-11-m-methyltriflouridebenzoate-spiroketal
1-methanol-11-m-nitrobenzoate-spiroketal

TABLE 3

1,11-dibenzoate-spiroketal
1-benzoate-11-m-methoxybenzoate-spiroketal
1-benzoate-11-p-methoxylbenzoate-spiroketal
1-benzoate-11-m-fluorobenzoate-spiroketal
1-benzoate-11-m-chlorobenzoate-spiroketal
1-benzoate-11-p-chlorobenzoate-spiroketal
1-benzoate-11-m-bromobenzoate-spiroketal
1-benzoate-11-p-bromobenzoate-spiroketal
1-benzoate-11-m-methyltriflouridebenzoate-spiroketal
1-benzoate-11-m-nitrobenzoate-spiroketal
1,11-di-m-methoxybenzoate-spiroketal
1-benzoate-1-m-methoxybenzoate-spiroketal
1-m-methoxybenzoate-11-p-methoxylbenzoate-spiroketal
1-m-methoxybenzoate-11-m-fluorobenzoate-spiroketal
1-m-methoxybenzoate-11-m-chlorobenzoate-spiroketal
1-m-methoxybenzoate-11-p-chlorobenzoate-spiroketal
1-m-methoxybenzoate-11-m-bromobenzoate-spiroketal
1-m-methoxybenzoate-11-p-bromobenzoate-spiroketal
1-m-methoxybenzoate-11-m-methyltriflouridebenzoate-spiroketal
1-m-methoxybenzoate-11-m-nitrobenzoate-spiroketal
1,11-di-p-methoxybenzoate-spiroketal
1-p-methoxybenzoate-11-m-methoxybenzoate-spiroketal

Example 7

Tubulin Depolymerization Activity of Libraries from Example 6

Figure 8A:
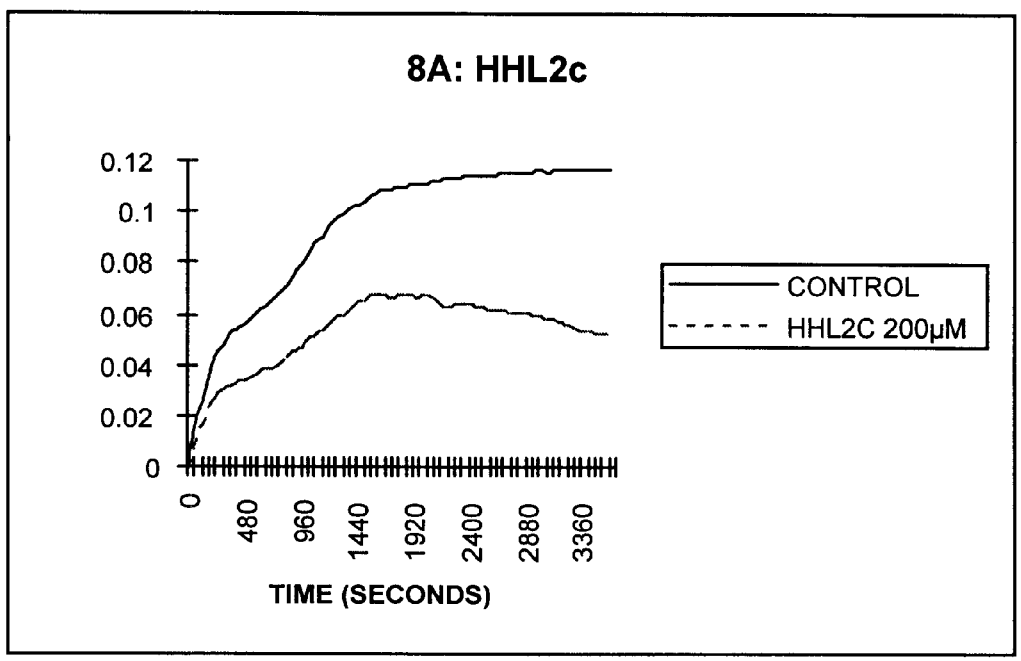
FIGS. 8A–8C are graphs showing the anti-tubulin effects of the library HHL2C (FIG. 8A), HHL2f (FIG. 8B), and HHL4c (FIG. 8C).
Figure 8B:
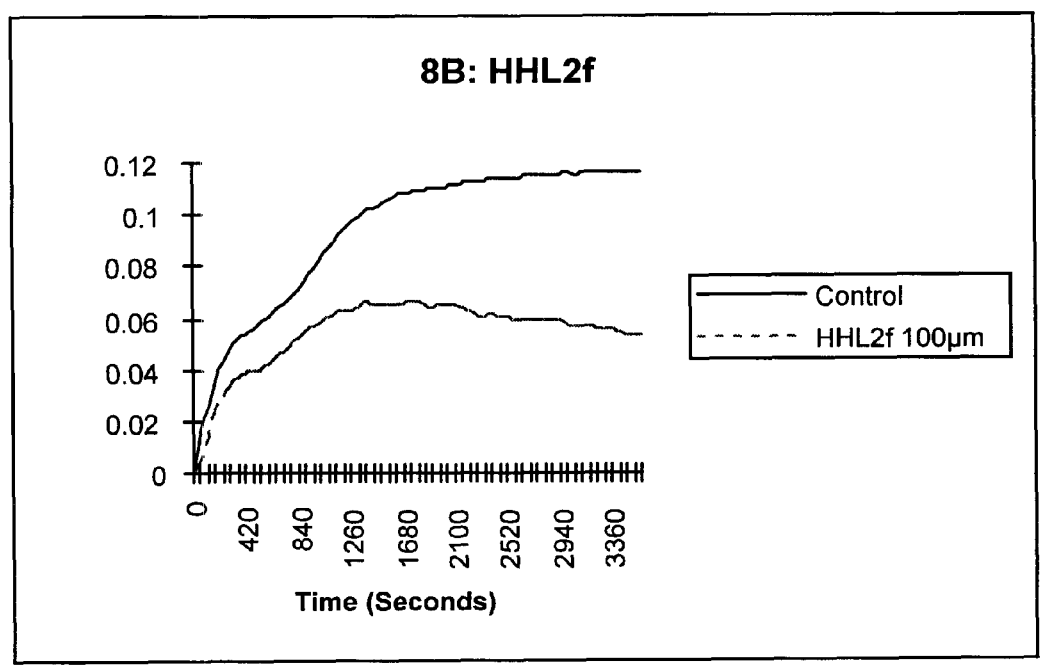
Figure 8C:
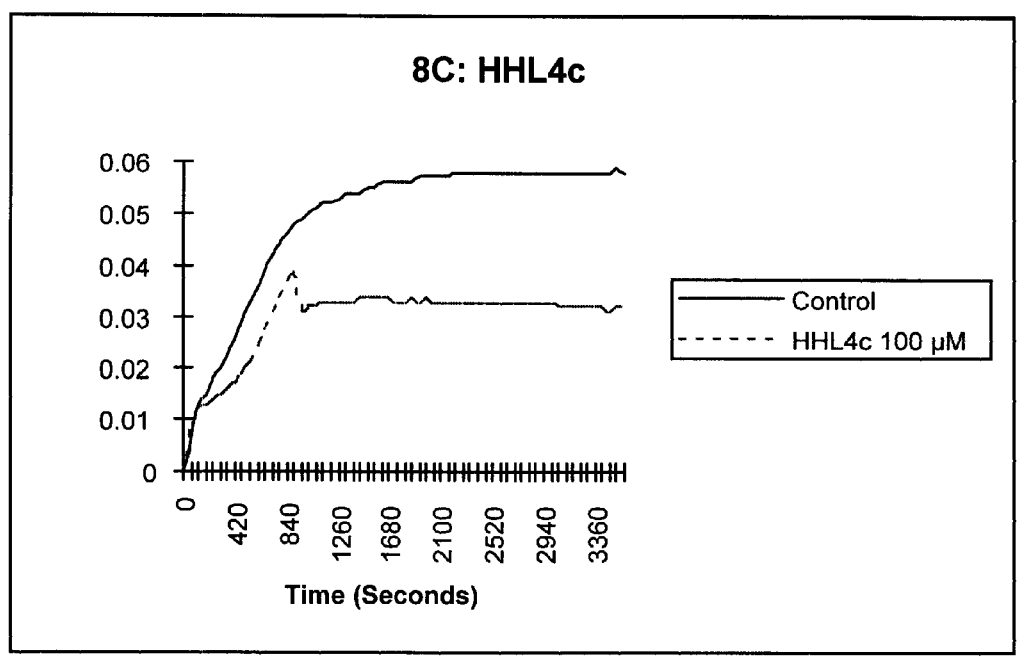

Turbidity assays were carried out on some of the libraries that were created in Example 6. The tubidity assays were completed using the materials and methods described in the Examples above. The results of the assays with the three libraries tested are shown in FIG. 8.

The SP biester library, HHL4c, exhibited potent tubulin depolymerizing activity in the tubulin turbidity assays (FIG. 8), superior to that of SPIKET-P1. These findings confirmed our hypothesis that simple modifications to the compounds of the invention can markedly improve the biologic activity of the novel SP pharmacophore SPIKET-P1.

All publications, patents, and patent documents described herein are incorporated by reference as if fully set forth. The invention described herein may be modified to include alternative embodiments. All such obvious alternatives are within the spirit and scope of the invention, as claimed below.

REFERENCES

1. Avila, J. *Life Sci.* 1992, 50, 327.
2. Hyams, J. S. and Lloyd, C. W. Microtubules 1994, New York.

3. Hyman, A. and Karsenti, E. *J Cell Sci.* 1998, 111 (Pt 15), 2077.
4. Downing, K. H. and Nogales, E. *Curr. Opit Cell Biol.* Feb. 10, 16 1998.
5. Kozielski, F., Arnal, I. and Wade, R. H. *Curr. Biol.* 1998, 8, 191.
6. Nogales, E., Wolf, S. G. and Downing, K. H. *Nature* 1998, 391, 199. 1993, 58, 1302.
8. Bai, R., Cichacz, Z. A., Herald, C. L., Pettit, G. R. and Hamel, E. *Molecular Pharmacology* 1993, 44, 757.
9. Bai, R., Taylor, G. F., Cichacz, Z. A., Herald, C. L., Kepler, J. A., Pettit, G. R. and Hamel, E. *Biochemistry* 1995, 34, 9714.
10. Nogales, E., Whittaker, M., Milligan, R. A. and Downing, K. H. *Cell* 1999, 96, 79.
11. Nicholls, A., Sharp, K. and Honig, B. *Protein, Structure, Function and Genetics* 1991, 11, 281ff.
12. Paterson, I., Oballa, R. M. and Norcross, R. D. *Tetrahedron Lett.* 1996, 37, 8581.
13. Uckun, F. M., Stewart, C. F., Reaman, G., Chelstrom, L. M., Jin, J., Chandan-Langlie, M., Waddick, K. G., White, J. and Evans, W. E. *Blood* 1995, 85, 2817.
14. Vassilev, A., Ozer, Z., Navara, C., Mahajan, S. and Uckun, F. M. *J Biol Chem.* Jan. 15, 1999 274(3), 164616.
15. Bohm, H. J. *J. Comput. Aided Mol. Des.* 1992, 6, 593.
16. Bohm, H. J. *J. Comput. Aided Mol. Des.* 1994, 8, 243.
17. Luty, B. A., Wasserman, P. F., Stouten, P. F., Hodge, C. N., Zacharias, M. and McCammon, J. A. *J. Comp. Chem.* 1995, 16, 454.
18. Vig, R., Mao, C., Venkatachalam, T. K., Tuel-Ahlgren, L., Sudbeck, E. A. and Uckun, F. M. *Bioorganic & Medicinal Chemistry* 1998, 6, 1.
19. Mao, C., Vig, R., Venkatachalam, T. K., Sudbeck, E. A. and Uckun, F. M. *Bioorganic & Medicinal Chemistry Letters* 1998, 8, 2213.
20. Connolly, M. L. *Science* 1983, 221, 709.
21. Corey, E. J. and Venkateswarlu *J. Am. Chem. Soc.* 1972, 94, 6190.
22. Danishefsky, S. J., Annistead, D. M., Wincott, F. E., Selnick, H. G. and Hungate, R. *J. Am. Chem. Soc.* 1987, 109, 8117.
23. Cohen, T., Jeong, I.-H., Mudryk, B., Bhupathy, M. and Awad, M. M. A. *J. Org. Chem.* 1990, 55, 1528.

We claim:

1. A compound having the structure of formula I:

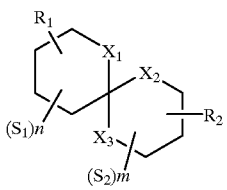

(I)

wherein:
at least one of $X^1$, $X^2$, and $X^3$ is O and the others are C;
$R^1$ and $R^2$ are the same or different and are each independently H, provided both $R^1$ and $R^2$ are not H, or $(C_1-C_8)$alkyl, $(C_1-C_8)$cycloalkyl, $(C_1-C_8)$alkoxy, $(C_1-C_8)$aryloxy, $(C_1-C_8)$arylthio, $(C_1-C_8)$aryl, $C(=)NR^aR^b$ or $NR^aR^b$; wherein $R^a$ and $R^b$ are each independently hydrogen, acyl, $(C_1-C_8)$alkyl, $(C_3-C_7)$cycloalkyl, $(C_6-C_{10})$aryl
n and m are the same or different, and are each independently 0 to 7;

$S^1$ and $S^2$ can be the same or different, and are each independently OH, SH, $CO_2H$, halogen, CN, acyl, thioacyl, ester, thioester, $(C_1-C_6)$alkoxy, $(C_1-C_6)$aryloxy, $(C_1-C_6)$alkylthio, $(C_1-C_6)$arylthio, $(C_1-C_6)$alkyl, $(C_1-C_6)$alkenyl, $(C_1-C_6)$alkynyl, $(C_3-C_7)$cycloalkyl, $(C_6-C_{10})$aryl, $C(=O)NR^aR^b$ or $NR^aR^b$; wherein $R^a$ and $R^b$ are each independently hydrogen, acyl, $(C_1-C_6)$alkyl, $(C_3-C_7)$cycloalkyl, $(C_6-C_{10})$aryl; taken together, any two $S^1$ and $S^2$ can form a ring, and any two adjacent substituents can form a double bond between the two carbons to which they are attached.

2. The compound of claim 1, wherein one or more of $R^1$, $R^2$, and $R^a$, and $R^b$ are substituted with at least one functional group selected from OH, SH, $CO_2H$, halogen, CN, acyl, thioacyl, ester, thioester.

3. The compound of claim 1, wherein at least one of $R^1$, $R^2$, $R^a$, and $R^b$ comprise an aromatic ring.

4. The compound of claim 1, wherein at least one of $R^1$, $R^2$, $R^a$, and $R^b$ is a group capable of hydrogen bonding wherein the group is —$(CH_2)_nOH$, n being 0–7, or $(C_1-C_6)$aryloxy.

5. The compound of claim 4, wherein said group is capable of hydrogen bonding with one or more residues of the spongistatin binding pocket selected from N101, E411, K105, and H406 of β tubulin.

6. The compound of claim 5, wherein said one or more group comprises a hydroxyl or alryoxy group.

7. The compound of claim 1, wherein one or more of $R^1$, $R^2$, $R^a$, and $R^b$ is capable of hydrophobic interaction with one or more hydrophobic residues of the spongistatin binding pocket selected from Y185, Y408, F399, F404, and W407 of tubulin.

8. The compound of claim 1, wherein one or more of $R^1$, $R^2$, $R^a$, and $R^b$ is capable of Van der Waals interactions with one or more hydrophobic residues of the spongistatin binding pocket selected from Y185, Y408, F399, F404, and W407 of tubulin.

9. The compound of claim 1, wherein one or more of $R_1$, $R^2$, $R^a$, and $R^b$ —$CH_2OH$.

10. The compound of claim 1, wherein one or more of $R_1$, $R^2$, $R^a$, and $R^b$ —$(CH_2)_nOH$, n being 0–7.

11. The compound of claim 1, wherein one or more of $R_1$, $R^2$, $R^a$, and $R^b$ —$CH_2$ $CH_2OPh$.

12. A compound having the structure of formula II:

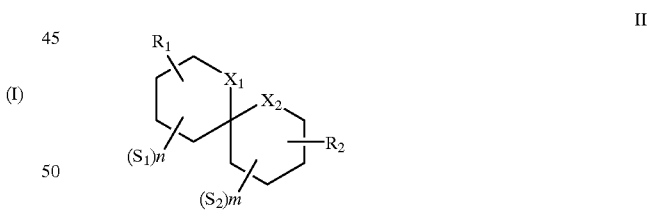

II wherein:
at least one or both of $X^1$, $X^2$ is O and, if only is O, the other is C;
$R^1$ and $R^2$ are the same or different and are each independently H, provided both $R^1$ and $R^2$ are not H, or $(C_1-C_8)$alkyl, $(C_1-C_8)$cycloalkyl, $(C_1-C_8)$alkoxy, $(C_1-C_8)$aryloxy, $(C_1-C_8)$arylthio, $(C_1-C_8)$aryl, $C(=)NR^aR^b$ or $NR^aR^b$; wherein $R^a$ and $R^b$ are each independently hydrogen, acyl, $(C_1-C_8)$alkyl, $(C_3-C_7)$cycloalkyl, $(C_6-C_{10})$aryl;
n and m are the same or different, and are each independently 0 to 7;
$S^1$ and $S^2$ can be the same or different, and are each independently OH, SH, $CO_2H$, halogen, CN, acyl, thioacyl, ester, thioester, $(C_1-C_6)$alkoxy, $(C_1-C_6)$aryloxy, $(C_1-C_6)$alkylthio, $(C_1-C_6)$arylthio, $(C_1-C_6)$alkyl, $(C_1-C_6)$alkenyl, $(C_1-C_6)$alkynyl, $(C_3-C_7)$cycloalkyl, $(C_6-C_{10})$aryl, $C(=O)NR^aR^b$ or $NR^aR^b$; wherein $R^a$ and $R^b$ are each independently hydrogen, acyl, $(C_1-C_6)$alkyl, $(C_3-C_7)$cycloalkyl, $(C_6-C_{10})$aryl; taken together, any two $S^1$ and $S^2$ can form a ring, and any two adjacent substituents can form a double bond between the two carbons to which they are attached.

13. The compound of claim 12, having the structure of formula VI:

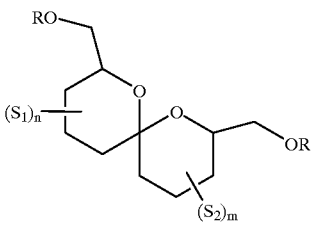

(VI)

where R is a group capable of hydrogen bonding wherein the group is —$(CH_2)_nOH$, n being 0–7, or $(C_1-C_6)$aryloxy.

14. A compound having the structure of formula III:

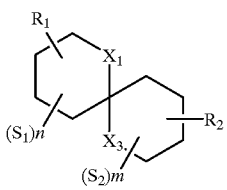

(III)

wherein:

at least one or both of $X^1$ and $X^3$ is O, and, if only one is O, the other is C; $R^1$ and $R^2$ are the same or different and are each independently H, provided both $R^1$ and $R^2$ are not H, or $(C_1-C_8)$alkyl, $(C_1-C_8)$cycloalkyl, $(C_1-C_8)$alkoxy, $(C_1-C_8)$aryloxy, $(C_1-C_8)$arylthio, $(C_1-C_8)$aryl, $C(=)NR^aR^b$ or $NR^aR^b$; wherein $R^a$ and $R^b$ are each independently hydrogen, acyl, $(C_1-C_8)$alkyl, $(C_3-C_7)$cycloalkyl, $(C_6-C_{10})$aryl;

n and m are the same or different, and are each independently 0 to 7;

$S^1$ and $S^2$ can be the same or different, and are each independently OH, SH, $CO_2H$, halogen, CN, acyl, thioacyl, ester, thioester, $(C_1-C_6)$alkoxy, $(C_1-C_6)$aryloxy, $(C_1-C_6)$alkylthio, $(C_1-C_6)$arylthio, $(C_1-C_6)$alkyl, $(C_1-C_6)$alkenyl, $(C_1-C_6)$alkynyl, $(C_3-C_7)$cycloalkyl, $(C_6-C_{10})$aryl, or $C(=O)NR^aR^b$ or $NR^aR^b$; wherein $R^a$ and $R^b$ are each independently hydrogen, acyl, $(C_1-C_6)$alkyl, $(C_3-C_7)$cycloalkyl, $(C_6-C_{10})$aryl taken together, any two $S^1$ and $S^2$ can form a ring, and any two adjacent substituents can form a double bond between the two carbons to which they are attached.

15. A compound having the formula IV or V:

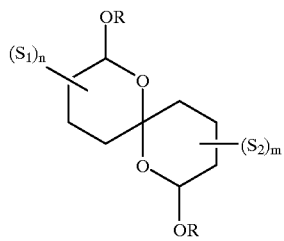

(IV)

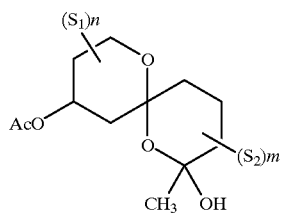

(V)

wherein:

$S^1$ and S2 can be the same or different, and are each independently OH, SH, $CO_2H$, halogen, CN, acyl, thioacyl, ester, thioester, $(C_1-C_6)$alkoxy, $(C_1-C_6)$aryloxy, $(C_3-C_6)$alkylthio, $(C_1-C_6)$arylthio, $(C_1-C_6)$akyl, $(C_1-C_6)$alkenyl, $(C_1-C_6)$alkynyl, $(C_3-C_7)$cycloalkyl, $(C_6-C_{10})$aryl, $C(=O)NR^aR^b$ or $NR^aR^b$; wherein $R^a$ and $R^b$ are each independently hydrogen, acyl, $(C_1-C_6)$alkyl, $(C_3-C_7)$cycloalkyl, $(C_6-C_{10})$aryl;

and wherein R is a group capable of hydrogen bonding wherein the group is —$(CH_2)_nOH$, n being 0–7, or $(C_1-C_6)$aryloxy.

16. The compound of the formula VI:.

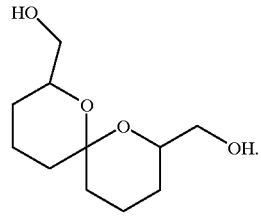

VI

17. The compound of the formula VII:.

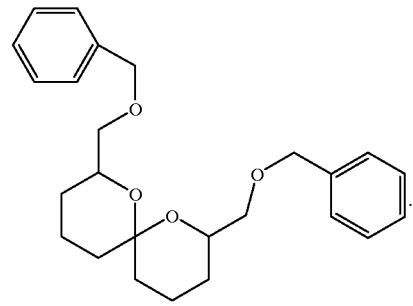

VII

* * * * *